United States Patent
Altare et al.

(10) Patent No.: US 12,405,267 B2
(45) Date of Patent: Sep. 2, 2025

(54) **DIAGNOSIS, PROGNOSIS AND TREATMENT OF A DISEASE RELATED TO A DECREASE OF *F. PRAUSNITZII***

(71) Applicants: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE D'ANGERS, Angers (FR); UNIVERSITE DE NANTES, Nantes (FR); ASSISTANCE PUBLIQUE—HOPITAUX DE PARIS, Paris (FR); SORBONNE UNIVERSITE, Paris (FR)

(72) Inventors: Frédéric Altare, Nantes (FR); Guillaume Sarrabayrouse, Barcelona (ES); Harry Sokol, Paris (FR); Emmanuelle Godefroy, Nantes (FR); Francine Jotereau, Nantes (FR)

(73) Assignees: INSTITUT NATIONAL DE LA SANTE ET DE LA RECHERCHE MEDICALE (INSERM), Paris (FR); CENTRE NATIONAL DE LA RECHERCHE SCIENTIFIQUE, Paris (FR); UNIVERSITE D'ANGERS, Angers (FR); UNIVERSITE DE NANTES, Nantes (FR); ASSISTANCE PUBLIQUE—HOPITAUX DE PARIS, Paris (FR); SORBONNE UNIVERSITÉ, Paris (FR)

( * ) Notice: Subject to any disclaimer, the term of this patent is extended or adjusted under 35 U.S.C. 154(b) by 1315 days.

(21) Appl. No.: 17/059,315

(22) PCT Filed: May 31, 2019

(86) PCT No.: PCT/EP2019/064210
§ 371 (c)(1),
(2) Date: Nov. 27, 2020

(87) PCT Pub. No.: WO2019/229247
PCT Pub. Date: Dec. 5, 2019

(65) Prior Publication Data
US 2021/0215676 A1    Jul. 15, 2021

(30) Foreign Application Priority Data
Jun. 1, 2018    (EP)    .................................... 18305677

(51) Int. Cl.
G01N 33/50    (2006.01)
A61K 40/11    (2025.01)
A61K 40/22    (2025.01)
A61K 40/40    (2025.01)
A61K 40/41    (2025.01)
A61K 40/45    (2025.01)
G01N 33/569    (2006.01)

(52) U.S. Cl.
CPC .......... *G01N 33/5091* (2013.01); *A61K 40/11* (2025.01); *A61K 40/22* (2025.01); *A61K 40/40* (2025.01); *A61K 40/416* (2025.01); *A61K 40/45* (2025.01); *G01N 33/505* (2013.01); *G01N 33/56911* (2013.01); *G01N 2800/065* (2013.01); *G01N 2800/52* (2013.01); *G01N 2800/56* (2013.01)

(58) Field of Classification Search
None
See application file for complete search history.

(56) References Cited

FOREIGN PATENT DOCUMENTS

WO    2015/004270 A1    1/2015
WO    WO 2015/004270    *    1/2015    ............. G01N 33/50

OTHER PUBLICATIONS

Mandai et al., "Distinct Roles for CXCR6+ and CXCR6-CD4+ T Cells in the Pathogenesis of Chronic Colitis", PLOS One, vol. 8, No. 6, Jun. 19, 2013.*
"Microbiota-specific CD4CD8αααα Tregs: role in intestinal immune homeostasis and implications for IBD", Sarrabayrouse et al., Front. Immunol. 6:522 (2015).*
"CD4CD8aa Lymphocytes, A Novel Human Regulatory T Cell Subset Induced by Colonic Bacteria and Deficient in Patients with Inflammatory Bowel Disease" Sarrabayrouse et al., PLoS Biol 12(4): e1001833 (2014).*
Das et al: "An Important regulatory role for CD4+CD8alpha alpha T cells in the intestinal epithelial layer in the prevention of inflammatory bowel disease", Proceedings of the National Academy of Sciences, vol. 100, No. 9, pp. 5324-5329, Apr. 29, 2003.

(Continued)

Primary Examiner — Ann Montgomery
(74) Attorney, Agent, or Firm — WCF IP

(57) ABSTRACT

The invention relates to a method comprising a step of determining the number, concentration and/or proportion of T lymphocytes with a $CD4^+$ $CD8\alpha\alpha^{low}$ phenotype and further expressing CCR6 and/or CXCR6, for (i) diagnosing, (ii) prognosing outcome of, or (iii) predicting the risk of developing a disease related to a decrease of *F. prau*. The invention also concerns the treatment of said disease by administering a population of these specific T lymphocytes. The Inventors have indeed identified two markers, CCR6 and CXCR6, enabling to select a population of *F. prau*-specific cells among $CD4^+$ $CD8\alpha\alpha^{low}$ T lymphocytes, from a blood sample and without needing to assess their *F. prau* specificity. T lymphocytes with a $CD4^+$ $CD8\alpha\alpha^{low}$ CCR6+ CXCR6+ phenotype are for example significantly decreased in IBD patients. The disease related to a decrease of *F. prau* is particularly an inflammatory bowel disease (IBD), such as Crohn's disease.

3 Claims, 10 Drawing Sheets
Specification includes a Sequence Listing.

(56) References Cited

OTHER PUBLICATIONS

Katchar et al: "MIP-3 alpha neutralizing monoclonal antibody protects against TNBS-induced colonic injury and inflammation in mice", American Journal of Physiology—Gastrointestinal and Liver Physiology, vol. 292, No. 5, pp. G1263-1271, May 1, 2007.
Mandai et al: "Distinct Roles for CXCR6+ and CSCR6-CD4+ T Cells in the Pathogenic of Chronic Colitis", PLOS One, vol. 8, No. 6, Jun. 19, 2013.
Sarrabayrouse et al: "CD4CD8[alpha][alpha] Lymphocytes, A Novel Human Regulatory T Cell Subset Induced by Colonic Bacteria and Deficient in Patients with Inflammatory Bowel Disease", PLOS One, vol. 12, No. 4, Apr. 8, 2014.
Senju et al: Coexpression of CD4 and CD8 on peripheral blood T cells and lamina propria T cells in inflammatory bowel disease by two colour immunofluorescence and flow cytometric analysis', Gut, vol. 32, No. 8, pp. 918-922, Aug. 1, 1991.
Sokol et al: "Faecalibacterium prausnitzii is an anti-inflammatory commensal bacterium identified by gut microbiota analysis of Crohn disease patients", National Academy of Sciences, vol. 105, No. 43, pp. 16731-16736, Oct. 28, 2008.
Varona et al: "CCR6 Has a Non-Redundant Role in the Development of Inflammatory Bowel Disease", European Journal of Immuno, vol. 33, No. 10, pp. 2937-2946, Oct. 1, 2003.
Wakahara, K. et al., "Human basophils interact with memory T cells to augment Th17 processes", Blood 120, No. 24, 2012.
Pardigon, N. et al., "CD8aa-Mediated Intraepithelial Lymphocyte Snatching of Thymic Leukemia MHC Class Ib Molecules In Vitro and In Vivo", The Journal of Immunology 177, 2006.

* cited by examiner

DIAGNOSIS, PROGNOSIS AND TREATMENT OF A DISEASE RELATED TO A DECREASE OF F. PRAUSNITZII

FIELD OF THE INVENTION

The invention relates to the diagnosis, prognosis and treatment of diseases related to a decrease of *F. prausnitzii*, more particularly of inflammatory bowel diseases (IBD).

BACKGROUND OF THE INVENTION

Various diseases, such as IBD (Inflammatory Bowel Disease) or metabolic disorders, involve dysregulated immune response against gut microbiota, which thus represents a major causal candidate, especially in IBD where its composition is imbalanced (i.e. dysbiosis) and may predict disease evolution. A common feature shared by most IBD patients lies in an overall decrease in major genera of the Firmicutes phylum, such as *Faecalibacterium* and *Roseburia* bacteria, which have been reported to convey anti-inflammatory effects in vitro and in vivo. This is especially the case for *Faecalibacterium prausnitzii* (*F. prau*), a member of the *Clostridium* IV group of the Firmicutes phylum that accounts for about 5% of the total fecal microbiota in healthy subjects, making it the most abundant microbiota bacterium. Changes in the abundance of *F. prau* and other members of the *Clostridium leptum* group have been extensively reported in different human intestinal and metabolic disorders. Importantly, in the context of IBD, *F. prau* is a potent inducer of IL-10 secretion, a cytokine known to be a master regulator of intestinal mucosal homeostasis in mice and humans. Together, these data suggest that low levels of *F. prau* among the microbiota might disturb the control of inflammatory responses.

Sarrabayrouse et al. (2014, PLOS Biol. 12 (4) e1001833) characterized, in the human colon lamina propria, a subset of Treg (T regulatory lymphocytes) whose reactivity against *F. prau* antigens suggested the contribution of this Clostridia to their induction. These results brought the first evidence that in humans, like in mice, *Clostridium* IV bacteria play a role in stimulating the generation of colon Treg. However, in contrast with mice data, these Treg lacked Foxp3 expression and exhibited a unique phenotype characterized by the stable co-expression of CD4 and of low levels of CD8a, but not CD8b. This cell subset was named "double positive CD8a" or DP8a. Remarkably, while DP8a lamina propria lymphocytes (LPL) lacked Foxp3, they shared most regulatory markers (CD25, GITR, CTLA-4 and LAG-3) and functions (inhibition of dendritic cell (DC) maturation and of T cell proliferation) with Foxp3-expressing Treg. Moreover, they were relatively abundant in the healthy colonic mucosa (13% of CD4 LPL) and were decreased in the inflamed colonic mucosa of Crohn's disease patients, suggesting a role for these cells in colon homeostasis.

Around 2% of circulating CD4 PBMCs display the DP8a phenotype. Whether these circulating cells strictly reflect the role of their colonic counterparts is unknown, even though about 10% of these cells recognized *F. prau* and thus likely represent recirculating colonic Treg. Additionally, circulating DP8a Treg appeared to be less frequent in the blood of IBD patients compared with healthy donors, suggesting these circulating cells indeed echo their function in the colon.

Document WO2015/004270 for example discloses methods for diagnosing, prognosing outcome of and predicting the risk of developing an IBD in a patient, wherein said methods comprise determining the number, concentration and/or proportion of these Treg with a CD4$^+$CD8αα$^{low}$ Foxp3$^{neg}$ phenotype, which are specific for *F. prau*. Document WO2015/004270 also discloses the use of Treg with a CD4$^+$ CD8αα$^{low}$ Foxp3$^{neg}$ phenotype, which are specific for *F. prau*, for treating IBD.

However, selecting and/or quantifying overall circulating DP8a cells specific for *F. prau* remains cumbersome. This bacterium is indeed difficult to grow, due to its anaerobic properties, and there is a need for autologous or HLA-matched antigen presenting cells.

There is therefore still a need for methods for prognosing, diagnosing and/or treating inflammatory bowel disease (IBD), which methods are non-invasive, reliable and/or easy to carry out.

DESCRIPTION OF THE INVENTION

The Inventors have found two markers, CCR6 and CXCR6, enabling to select a population of *F. prau*-specific DP8a cells among DP8a cells. Advantageously, by using CCR6 and/or CXCR6, the colonic homeostasis or inflammation status of a subject may be assessed directly from a blood sample and without needing a step of assessing the specificity of circulating DP8a cells for *F. prau*.

The Inventors indeed showed a significant decrease of the DP8a cells expressing CCR6 and CXCR6 in IBD patients, underlying the interest of these markers for the diagnosis and clinical follow-up of IBD patients. Importantly, CCR6 and CXCR6 allow discriminating an IBD from an infectious colitis, which was so far not possible at the time of the first IBD flare.

By using CCR6 and/or CXCR6, improved methods are provided for selecting *F. prau*-specific DP8a cells, and thus for the diagnosis, prognosis, prevention and/or treatment of a disease characterized by a decrease of *F. prau.*, such as IBD and also for the stratification of a subject suffering from or at risk of developing a disease potentially associated with a decrease of *F. prau* in the gut microbiote.

These new methods are indeed non-invasive, reliable and easy to carry out and faster, since the analysis (i) can be performed starting from a blood sample rather than colonic biopsies where very little material ends up being available and (ii) does not require to culture *F. prau*, nor to provide autologous or HLA-matched antigen presenting cells analysis.

A first object of the invention is thus a method for selecting T regulatory lymphocytes with a CD4$^+$ CD8αα$^{low}$ phenotype which are specific for *F. prausnitzii* in a biological sample, wherein said method comprises selecting cells with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6+CXCR6$^+$ phenotype.

Said method may for example comprise the steps of:
a) optionally, selecting cells expressing CD3, to obtain T lymphocytes,
b) selecting cells expressing both CD4 and CD8αα$^{low}$, to obtain DP8a T regulatory lymphocytes,
c) selecting, particularly among the DP8a T regulatory lymphocytes obtained in step b), the cells expressing CCR6 and/or CXCR6.

Another object of the invention is a method of determining if a subject is afflicted with a disease characterized by a decrease of *F. prausnitzii*, wherein said method comprises:
a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the subject, b) optionally, comparing the result of step a) with i) a control standard value corresponding to the number and/or concentration and/or proportion of these T lymphocytes typically found in a biological sample of the same nature from a healthy subject, and/or ii) a control standard value corresponding to the number and/or concentration and/or proportion of these T lymphocytes typically found in a biological sample of the same nature from a patient suffering from said disease characterized by a decrease of F. prausnitzii; and c) deducting from the result(s) of step a) and/or step b) where appropriate, if the subject is afflicted with a disease characterized by a decrease of F. prausnitzii.

Another object of the invention is a method of prognosing outcome of a disease characterized by a decrease of F. prausnitzii in a patient suffering from said disease, wherein said method comprises:

a) a step of determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the patient, and b) deducting from the result of step a) the prognosis of said patient.

Another object of the invention is a method of predicting whether a subject is at risk of developing a disease characterized by a decrease of F. prausnitzii, wherein said method comprises:

a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the subject;

b) predicting from the result of step a) if the subject is at risk of suffering from a disease characterized by a decrease of F. prausnitzii.

Another object of the invention is a method of monitoring the efficacy of a preventive or curative treatment of a disease characterized by or associated with a decrease of F. prausnitzii, wherein the method comprises a step of monitoring the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the subject during the treatment.

In the above methods, the disease characterized by a decrease of F. prausnitzii is particularly inflammatory bowel disease (IBD), particularly Crohn's disease and/or ulcerative colitis.

In the above method, the disease associated with a decrease of F. prausnitzii is for example allergy, obesity, colon cancer, Graft Versus Host Disease (also called GvHD) and/or a disease wherein the decrease of F. prausnitzii results from a treatment.

Another object of the invention is a pharmaceutical composition comprising isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype Another object of the invention is T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype for use as a medicament in a method for preventing and/or treating a disease characterized by a decrease of F. prausnitzii or a disease associated with a decrease in F. prau.

Another object of the invention is a method for the stratification of a subject suffering from or at risk of developing a disease potentially associated with a decrease of F. prausnitzii into a category of subjects with a decrease of F. prausnitzi or a category of subjects with standard level of F. prausnitzii, wherein said method comprises:

a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the subject, b) optionally, comparing the result of step a) with i) a control standard value corresponding to the number and/or concentration and/or proportion of these T lymphocytes typically found in a biological sample of the same nature from a healthy subject, and/or ii) a control standard value corresponding to the number and/or concentration and/or proportion of these T lymphocytes typically found in a biological sample of the same nature from a patient suffering from said disease characterized by a decrease of F. prausnitzii; and c) from the result(s) of step a) and/or step b) where appropriate, stratifying the subject into a category of subjects with a decrease of F. prausnitzi or a category of subjects with standard level of F. prausnitzii.

In the above methods, the biological sample is particularly a blood sample, for example total blood or a blood fraction comprising peripheral blood mononuclear cells (PBMC) and/or peripheral blood lymphocytes (PBL).

Another object of the invention is a kit for diagnosing, prognosing and/or predicting the risk of developing a disease characterized by a decrease of F. prausnitzii and/or for monitoring the efficacy of a treatment of a disease characterized by a decrease of F. prausnitzii and/or for selecting T regulatory lymphocytes with a CD4$^+$ CD8αα$^{low}$ phenotype which are specific for F. prausnitzii, wherein said kit comprises means for determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype.

Said kit may for example comprises:
at least one antibody or fragment thereof specific for CCR6 and/or at least one antibody specific for CXCR6,
at least one antibody or fragment thereof specific for CD4,
at least one antibody or fragment thereof specific for CD8a, and
optionally, at least one antibody of fragment thereof specific for CD3.

Definitions

As used herein, a "biological sample" may comprise or consist of a colonic mucosa sample, a biopsy sample from the gastrointestinal tract, a colonic biopsy sample, a small intestine biopsy sample and/or a blood sample.

A preferred biological sample is a blood sample.

Before being used or analyzed, the blood sample may be submitted to at least one treatment step, such as elutriation, adding an anticoagulant, for example adding EDTA, centrifugation, such as Ficoll gradient, dilution, heat or cold treatment, adding at least one reagent other than an anticoagulant and their combinations.

Alternatively, the blood sample is used directly, i.e. untreated.

A blood sample may for example be total blood or a blood fraction.

A blood fraction particularly comprises or consists of the peripheral blood mononuclear cells (PBMC) and/or peripheral blood lymphocytes (PBL) from the blood sample.

The expressions "T regulatory lymphocytes with a CD4$^+$ CD8αα$^{low}$ phenotype", "T regulatory lymphocytes characterized by a CD4$^+$ CD8αα$^{low}$ phenotype", "DP8α Treg" "DP8a Treg", "DP8a cells" and "DP8a T regulatory lymphocytes" are used interchangeably and refer to lymphocytes, which express and display at their surfaces at least the cluster of differentiation molecules CD3 and CD4, and the cluster of differentiation molecule CD8a consisting of the α/α homodimer, the level of expression of which being lower than that on T lymphocytes expressing the cluster of differentiation molecule CD8 consisting of the α/β heterodimer.

The expressions "cell with a CD8αα$^{low}$ phenotype" and "cell expressing CD8αα$^{low}$" are used interchangeably and thus mean that said cell expresses the homodimer α/α in a quantity lower than the quantity of chain a expressed by a T lymphocyte with a CD8α/β phenotype. Besides, a cell with a CD8αα$^{low}$ phenotype does not express the heterodimer α/β.

DP8α Treg are also characterized by a lack of expression of Foxp3 (called "Foxp3$^{neg}$" or "Foxp3" T lymphocytes).

Upon activation, DP8a Treg particularly secrete at least IFN-γ and interleukin-10 (IL-10), little if any IL-2. Upon activation, these cells preferably do not express IL-17. In particular, depending on the activation, these cells do not express IL-4, IL-5, IL-13, IL-17 and/or IL-22, for example do not express IL-4, IL-5, IL-13, IL-17 and IL-22. Upon polyclonal activation, these cells may express IL-4, IL-5, IL-13 and/or IL-22.

DP8a Treg may be cells from a subject, primary culture cells or cells from an established cell line or from a clone, said cell line or clone being particularly derived from primary culture cells.

The DP8a Treg may be lamina propria lymphocytes (hereinafter abbreviated as "LPL"), peripheral blood lymphocytes (PBL), peripheral blood mononuclear cells (PBMC), lymphocytes derived from naïve CD4 T cells or established cell lines derived therefrom.

In a preferred embodiment, DP8a Treg are peripheral blood lymphocytes (PBL) and/or peripheral blood mononuclear cells (PBMC).

LPL are particularly obtained from a tissue sample of colonic mucosa.

LPL may be obtained by any suitable method well known by the skilled person.

A process for obtaining LPL may comprise the following steps:
- separation of the lamina propria from the epithelium in a tissue sample of colonic mucosa, to obtain an isolated lamina propria,
- digestion of the isolated lamina propria with collagenase and DNAse, to obtain a digested lamina propria,
- filtration of the digested lamina propria, to obtain cells of the lamina propria free of mucus and large debris, and centrifugation of said cells of the lamina propria, to obtain viable cells of the lamina propria, and
- selection of the LPL, for example by selecting cells expressing the surface marker CD3 or by selective culture.

The separation of the Lamina propria (LP) from the epithelium in the tissue sample of colonic mucosa is for example carried out by incubating the tissue sample under agitation in EDTA buffer, for example for 30 minutes, followed by stripping and washing in a buffer, for example PBS. The lamina propria thereby isolated is then minced into 1 mm$^2$ fragments and washed with culture medium, for example RPMI containing penicillin (10%) and gentamycin (0.1 mg/ml; Sigma-Aldrich). Said tissue fragments are then digested with collagenase and DNAse (2 mg/ml each; Sigma-Aldrich), with shaking at 37° C. Mucus and large debris are removed by filtration through a 40-μm-cell strainer (BD). Viable cells are then obtained by Ficoll gradient centrifugation. LPL may then be selected by selecting cells expressing the surface marker CD3 or by a selective culture. An example of selective culture for obtaining lymphocytes is a culture wherein cells are stimulated with PHA (phytohemagglutinin) in the presence of irradiated feeder cells.

PBL may be obtained by any suitable method well-known by the skilled person. For example, PBL are obtained from a blood sample by elutriation.

PBL may also be isolated form PBMC.

PBMC (Peripheral Blood Mononuclear Cell) may be obtained by any suitable method well-known by the skilled person. For example, PBMCs are obtained from a blood sample, particularly a blood sample comprising an anticoagulant, such as EDTA, by Ficoll gradient centrifugation.

The term "isolated" or "purified" with regard to a population of DP8a Treg as used herein refers to a cell population which either has no naturally-occurring counterpart or has been separated or purified from other components, including other cell types, which naturally accompany it, e.g., in normal or diseased tissues such as colon tissue, or body fluids such as blood. Typically, an isolated cell population is at least two-fold, four-fold, eight-fold, ten-fold, twenty-fold or more enriched for DP8a Treg when compared to the natural source from which the population was obtained. In an isolated population of DP8a T regulatory lymphocytes, the number of DP8a T regulatory lymphocytes represents at least 50%, 75%, 80%, 90%, 95% or, most particularly, at least 96%, 97%, 98% or 99% of the total cell number of the population.

Isolating DP8a T regulatory lymphocytes (or a population of DP8a T regulatory lymphocytes) can be performed by using selective expression of surface markers unique to these cells. In particular, DP8a T regulatory lymphocytes may be sorted in a first time through positive selection of the cell surface protein CD4, the cell surface protein CD8 a/a at low levels and, optionally the cell surface protein CD3.

Methods for carrying out selection based on the presence or the absence of cell surface proteins are well-known to one skilled in the art. For instance, these cells may be isolated, i.e. purified, by immunologic selection using antibodies which selectively bind to a selected cell surface protein.

The term "immunologic selection" refers to selecting and, optionally, quantifying the number of cells displaying or not specific cell surface proteins, for example from a sample, particularly by specific binding of said proteins to an antibody or fragment thereof specific to said protein(s). Preferred immunologic selection methods useful in the methods of the present invention include cell staining, flow cytometry, fluorescence-activated cell sorting (FACS), magnetic bead purification (using magnetic beads coated with antibodies directed against a selected cell surface antigen) and the like.

In the context of the invention, the DP8α Treg are specific for *F. prausnitzii* (also called *F. prausnitzii*-induced DP8α Treg), i.e. they express T-cell receptors specific for *F. prausnitzii*, so that they react specifically to antigen-presenting cells loaded with *F. prausnitzii*.

A previously disclosed immunologic method to detect DP8x Treg specific for *F. prausnitzii* is based on the selection of DP8α lymphocytes responding to (i) an APC loaded with the bacteria *F. prau* or a fragment of *F. prau*.

The term "antigen-presenting cell" (hereinafter abbreviated as "APC") is herein intended to mean a cell that, after engulfing/internalizing and processing an antigen, displays the processed antigen complexed with major histocompatibility complexes (MHC) on their surfaces. The APCs may be recombinant APCs, for example artificial recombinant APCs. In particular, the APCs used in the present invention may be professional APCs, more particularly Dendritic cells, Macrophages, Monocytes, gamma-delta T lymphocytes (Himoudi. *J Immunol.*, 188(4):1708-16, 2012), EBV-transformed cell lines, as well as B-lymphocytes which express a B-cell receptor specific for an antigen of *F. prausnitzii* and which is able to further internalize and present this antigen at its surface associated with a class II MHC molecule. APCs useful in the present invention can also be non-professional APCs. Non-professional APCs do not constitutively express the major histocompatibility complexes, but stimulating with the appropriate cytokines triggers expression of class II MHC molecules. Non-professional APCs, together with the methods of stimulating them so that they express class II MHC molecules at their surfaces, are well known to the person of ordinary skill in the art, and are for instance described by Sundstrom J B and Ansari AA, *Transpl Immunol*, 4:273-289, 1995.

In the context of the invention, an "APC loaded with *F. prausnitzii*" and an "APC loaded with a fragment of *F. prausnitzii*" mean that an APC was incubated with *F. prausnitzii* or with a fragment of this bacteria or with a protein or peptide of the bacteria respectively, under culture condition and for a time sufficient to allow the *F. prausnitzii*, fragment, protein or peptide, where appropriate, to be internalized and processed by the APC, and then to allow the processed antigens from *F. prausnitzii* or from the fragment, protein or peptide of this bacteria to be displayed associated with major histocompatibility complexes, for instance MHC class II (MHC II), on the surface of the APC.

"*Faecalibacterium prausnitzii*" (abbreviated as "*F. prausnitzii*" or *F. prau*) is a commensal bacterium of the human gut flora classified in the Firmicutes phylum, Clostridia class, Clostridiales order, Clostridiaceae family and *Faecalibacterium* genus. This term refers to any strain of *Faecalibacterium prausnitzii*.

By "a *Faecalibacterium prausnitzii* strain" is meant any bacterium which belongs to the *Faecalibacterium prausnitzii* species.

The term "isolated" or "purified" with regard to *F. prausnitzii* refers to a population of *F. prausnitzii* with a purity of at least 50%, or by order of preference of at least 75%, 80%, 90%, 95%, 98%, 99%, or more particularly of 100%, the percentage being expressed as the number of *F. prausnitzii* per the number of bacteria.

In the context of the invention, the term "immunogenic fragment" when referring to *F. prausnitzii* (e.g. live, live-attenuated or killed *F. prausnitzii*) is intended to mean any part of *F. prausnitzii* (e.g. cell wall or a component thereof, such as peptidoglycan and/or proteins and/or peptides) that, once loaded by APC, allows a processed antigen from the fragment to form a complex with major histocompatibility complexes, in particular CMHII, said complex being displayed at the surface of the APC so that it can activate, i.e. trigger, expansion of DP8a Treg via TCR recognition.

In the context of the invention, the expression "proportion of" with regard to specific cells (for example T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype or with a $CD4^+$ $CD8\alpha\alpha^{low}$ $CCR6^+$ $CXCR6^+$ phenotype) is intended to mean the percentage of these specific cells relative to a whole population of given cells. For instance, the proportion of T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype or with a $CD4^+$ $CD8\alpha\alpha^{low}$ $CCR6^+$ $CXCR6^+$ phenotype, may be the percentage of these cells relative to the whole population of T lymphocytes or to the whole population of $CD4^+$ T cells.

As used herein, the terms "subject", "individual" and "patient" denote a human.

By "subject in need", it is herein meant an individual suffering from or susceptible of suffering from a disease characterized by a decrease of *F. prau*, an individual at risk for developing a disease characterized by a decrease of *F. prau*, or an individual that is in remission after having suffered from a disease characterized by a decrease of *F. prau*.

By "disease characterized by a decrease of *F. prau*", it herein means a disease resulting from and/or correlated with a reduced number or proportion of *F. prau* in the gut microbiota or the gut mucosa by comparison to the number or proportions found in the majority of healthy individuals.

A disease characterized by a decrease of *F. prau* is particularly IBD and/or a disease at high risk of being developed in an IBD patient, such as colon cancer.

A disease characterized by a decrease of *F. prau* which can be treated by the methods disclosed herein is particularly IBD.

A disease characterized by a decrease of *F. prau* which can be prevented by the methods disclosed herein is particularly IBD and/or a disease at high risk of being developed in an IBD patient, such as colon cancer.

The term "Inflammatory Bowel Disease", also called "IBD" refers to a group of inflammation conditions characterized by a chronic and relapsing inflammation of the gastrointestinal tract, for example as described by Baumgart and Sandbom (*Lancet*, 369:1641-1657, 2007). In the context of the invention, the IBD is particularly a Crohn's disease or an ulcerative colitis. More particularly, the IBD is a Crohn's disease.

By the expression "disease potentially associated with a decrease of *F. prau*", it herein means a disease characterized in that a particular category of patients suffering from said disease has a decrease in *F. prau*. In this particular category of patients, the disease is referred to as a disease associated with a decrease of *F. prau*.

A disease potentially associated with a decrease of *F. prau* is particularly selected in the group consisting of allergy, obesity, colon cancer, Graft Versus Host Disease (also called GvHD), a disease wherein the decrease of *F. prausnitzii* results from a treatment and their combinations.

Obesity may be associated or not with type 2 diabetes or pre-diabetic stage.

A disease associated with a decrease of *F. prau* which can be treated and/or prevented by the methods disclosed herein and/or the efficacy of a treatment of a disease associated with a decrease of *F. prau* may monitored by the methods disclosed herein.

A disease wherein the decrease of *F. prausnitzii* results from a treatment may be, for example at an early stage, a state characterized by a decrease of *F. prausnitzii*, without any other symptoms.

A treatment, which may result in a decrease in *F. prausnitzii* is for example an antibiotic treatment and/or a chemotherapy.

The expressions "healthy subject" and "healthy individual" are synonymous and refer to a subject who is not afflicted with a disease characterized by a decrease of *F. prau*. A healthy subject thus does not suffer from IBD, cancer and obesity, and, particularly, does not suffer from any allergy. Said healthy subject has preferably never been transplanted.

By the term "treating", it is herein meant a therapeutic method, for example a method aiming at curing, improving the condition and/or extending the lifespan of an individual suffering from a disease characterized by a decrease of *F. prau*, such as IBD.

By the term "preventing", it is herein meant a method aiming at preventing the appearance of a disease characterized by a decrease of *F. prau*, as well as a method aiming at preventing a relapse, such as IBD or cancer, particularly colon cancer.

As used herein, where applied to IBD or colon cancer, the term "preventing" is intended to mean that the onset of IBD or colon cancer is delayed or prevented.

Preventing and/or treating IBD may particularly result in preventing colon cancer.

By "effective amount" is meant an amount sufficient to achieve a concentration of compound which is capable of treating and/or preventing the disease to be treated and/or prevented. Such concentrations can be routinely determined by those of skilled in the art.

The amount of the compound actually administered will typically be determined by a physician, in the light of the relevant circumstances, including the condition to be treated, the chosen route of administration, the actual compound administered, the age, weight, and response of the individual patient, the severity of the patient's symptoms, etc.

As used herein, the term "at risk of developing a disease" denotes a higher trend to suffer from said disease in the future.

By "CCR6" or "CCR6 protein", also referred to as "Chemokine receptor 6", "CD196" or "cluster of differentiation 196", it is herein meant a CC chemokine receptor protein encoded by the CCR6 gene.

CCR6 is expressed on the cell surface.

A reference sequence for human CCR6 protein is for example SEQ ID NO: 1, which corresponds to the protein of reference AAB57794.1 in GenBank database, as available on Jul. 31, 2017.

CCR6 may comprise or consist of a sequence at least 80% identical to sequence SEQ ID NO: 1, particularly at least 85% identical, more particularly at least 90% identical, still more particularly at least 95%, at least 96%, at least 97%, at least 98% or at least 99% identical to sequence SEQ ID NO: 1.

CCR6 may for example comprise or consist of sequence SEQ ID NO: 1.

Antibodies specific for CCR6 are well known by the skilled person.

Antibodies specific for CCR6 for example include CCR6-BV421 (clone 11A9, BD Horizon).

By "CXCR6" or "CXCR6 protein", also referred to as "C-X-C chemokine receptor type 6", "CD186" or "cluster of differentiation 186", it is herein meant a chemokine receptor that is encoded by the CXCR6 gene.

CXCR6 is expressed on the cell surface.

A reference sequence for human CXCR6 protein is for example SEQ ID NO: 2, which corresponds to the protein of reference NP_006555.1 in the NCBI database, as available on Jul. 31, 2017.

CXCR6 may comprise or consist of a sequence at least 80% identical to sequence SEQ ID NO: 2, particularly at least 85% identical, more particularly at least 90% identical, still more particularly at least 95%, at least 96%, at least 97%, at least 98% or at least 99% identical to sequence SEQ ID NO: 2.

CXCR6 may for example comprise or consist of sequence SEQ ID NO: 2.

Antibodies specific for CXCR6 are well known by the skilled person and for example include CXCR6-APC (clone K041E5, Biolegend).

By "a sequence at least x % identical to a reference sequence", it is herein intended that the sequence is identical to the reference sequence or differ from the reference sequence by up to 100-x amino acid alterations per each 100 amino acids of the reference sequence.

The alignment and the determination of the percentage of identity may be carried out manually or automatically using for instance the Needle program which is based on the Needleman and Wunsch algorithm, described in Needleman and Wunsch (1970) J. Mol Biol. 48:443-453, with for example the following parameters for polypeptide sequence comparison: comparison matrix: BLOSUM62, gap open penalty: 10 and gap extend penalty: 0.5, end gap penalty: false, end gap open penalty=10, end gap extend penalty=0.5

As defined herein, an amino acid sequence "at least 80%, 85%, 90%, 95%, 96%, 97%, 98% or 99% identical" to a reference sequence may comprise mutations, such as deletions, insertions and/or substitutions compared to the reference sequence.

In case of substitutions, the substitution particularly corresponds to a conservative substitution as indicated in the Table 1 below. In a preferred embodiment, the sequence at least 80%, 85%, 90%, 95%, 96%, 97%, 98% or 99% identical to a reference sequence only differs from the reference sequence by conservative substitutions.

In another preferred embodiment, the amino acid sequence at least 80%, 85%, 90%, 95%, 96%, 97%, 98% or 99% identical to a reference sequence corresponds to a naturally-occurring variant of the reference sequence.

In a preferred embodiment, the amino acid sequence at least 80%, 85%, 90%, 95%, 96%, 97%, 98% or 99% identical to a reference sequence differs from the reference sequence by conservative substitution(s) and/or corresponds to a naturally-occurring variant of the reference sequence.

TABLE 1

| Conservative substitutions | Type of Amino Acid |
| --- | --- |
| Ala, Val, Leu, Ile, Met, Pro, Phe, Trp | Amino acids with aliphatic hydrophobic side chains |
| Ser, Tyr, Asn, Gln, Cys | Amino acids with uncharged but polar side chains |
| Asp, Glu | Amino acids with acidic side chains |
| Lys, Arg, His | Amino acids with basic side chains |
| Gly | Neutral side chain |

Method for Selecting T Regulatory Lymphocytes with a CD4+ CD8αα$^{low}$ Phenotype which are Specific for *F. prausnitzii*

The present invention provides a method enabling to easily select T regulatory lymphocytes with a CD4+ CD8αα$^{low}$ phenotype and which are specific for *F. prausnitzii*, without the need to assess the specificity to *F. prau*, for example by culturing the cells.

The present invention thus relates to a method, particularly an in vitro method, for selecting T regulatory lymphocytes with a CD4+ CD8αα$^{low}$ phenotype which are specific for *F. prausnitzii* in a biological sample, wherein said method comprises selecting cells with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype in said biological sample.

In a preferred embodiment of the invention, the method comprises selecting cells with a CD4+ CD8αα$^{low}$ CXCR6+ phenotype, more particularly cells with a CD4+ CD8αα$^{low}$ CCR6+ CXCR6+ phenotype.

Cells with a phenotype CD4+ CD8αα$^{low}$ are DP8a Treg.

Cells with a CD4+ CD8αα$^{low}$ CCR6+ phenotype are DP8a T regulatory lymphocytes expressing CCR6.

Cells with a CD4+ CD8αα$^{low}$ CXCR6+ phenotype are DP8a T regulatory lymphocytes expressing CXCR6.

Cells with a CD4+ CD8αα$^{low}$ CCR6+ CXCR6+ phenotype are DP8a T regulatory lymphocytes expressing CCR6 and CXCR6.

The population of cells with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype is correlated to, but is not strictly identical to a population of T regulatory lymphocytes with a CD4+ CD8αα$^{low}$ phenotype and which are specific for *F. prausnitzii*, this specificity being assessed by contacting DP8a Treg with APCs loaded with *F. prausnitzii* or fragments of *F. prausnitzii* under conditions which allow cells specific to *F. prausnitzii* to be activated.

Cells with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype consist of or comprise essentially DP8a T regulatory lymphocytes which are specific for *F. prausnitzii*.

The step of selecting cells with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype particularly comprises or consists of:
 a) optionally, selecting cells expressing CD3, to obtain T lymphocytes,
 b) selecting cells expressing both CD4 and CD8αα$^{low}$, to obtain DP8a T regulatory lymphocytes,
 c) selecting, particularly among the DP8a T regulatory lymphocytes obtained in step b), the cells expressing CCR6 and/or CXCR6, and
 d) optionally, determining the number and/or concentration and/or proportion of the cells expressing CCR6 and/or CXCR6 obtained in step c).

The step a) of selecting cells expressing CD3 is optional. When carried out, step a) improves the yield of selection, i.e. allows increasing the number of the selected cells having a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype.

When carried out, step a) is particularly performed before steps b) and c).

When carried out, step a) is performed on a biological sample as defined above, particularly a blood sample, such as total blood or blood fraction.

In step b), the cells expressing both CD4 and CD8αα$^{low}$ are particularly selected among cells from a biological sample as defined above, particularly a blood sample, such as total blood or a blood fraction, or among T lymphocytes, for example the T lymphocytes obtained in step a).

Cells expressing both CD4 and CD8αα$^{low}$ are cells:
 expressing CD4, and
 expressing CD8a in a quantity lower than those of the T lymphocytes expressing the cluster of differentiation molecule CD8 consisting of the α/β heterodimer, for example in a quantity lower than those of T lymphocytes CD4– and CD8α+.

In step c), the cells expressing CCR6 and/or CXCR6 cells are particularly selected among the DP8a Treg obtained in step b) or those obtained in step a) if step a) is carried out after step b).

Step c) is particularly performed after step b).

Alternatively, step c) may be performed before step a) and/or step b).

In a preferred embodiment, the cells selected in step c) are cells expressing CXCR6, more particularly cells expressing both CCR6 and CXCR6.

The selected cells with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype may be isolated to obtain isolated cells and/or may be quantified in order to determine their number and/or concentration and/or proportion.

Step d) consisting in determining the number and/or concentration and/or proportion of the cells expressing CCR6 and/or CXCR6 obtained in step c) is optional.

When step d) is carried out, steps c) and d) may be simultaneous or not.

When carried out, step d) thus allows determining the number and/or concentration and/or proportion of T regulatory lymphocytes with CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype.

The present invention thus also relates to a method for determining the number and/or concentration and/or proportion of T regulatory lymphocytes with CD4+ CD8αα$^{low}$ CCR6+ phenotype, a CD4+ CD8αα$^{low}$ CXCR6+ phenotype or a CD4+ CD8αα$^{low}$ CCR6+ CXCR6+, wherein said method comprises:
 a) optionally, selecting cells expressing CD3, to obtain T lymphocytes,
 b) selecting cells expressing both CD4 and CD8αα$^{low}$, to obtain DP8a T regulatory lymphocytes,
 c) selecting, particularly among the DP8a T regulatory lymphocytes obtained in step b), the cells expressing CCR6 and/or CXCR6, and
 d) determining the number and/or concentration and/or proportion of the cells expressing CCR6 and/or CXCR6 obtained in step c).

Steps a) to d) are particularly as defined above.

The step of determining the number and/or concentration and/or proportion of T regulatory lymphocytes with CD4+ CD8αα$^{low}$ CCR6+ phenotype, a CD4+ CD8αα$^{low}$ CXCR6+ phenotype or a CD4+ CD8αα$^{low}$ CCR6+ CXCR6+ is for example carried out by flow cytometry.

When the selected specific cells are isolated in the above methods, the selection is particularly an immunologic selection, for example by immunosorting.

Methods of immunosorting using labelled-antibodies or labelled fragments of antibodies specific to the proteins displayed at the surface of cells of interest are particularly suitable for quantifying these cells of interest. These methods are known in the art. Preferred immunologic selection/immunosorting methods useful in the method of the invention include flow cytometry, in particular Fluorescence-activated cell sorting (FACS).

The claimed methods do not require anymore and thus do not comprise a step of determining the number of the DP8a Treg, which are specific to *F. prausnitzii*, for example by contacting DP8a Treg with APCs loaded with *F. prausnitzii* or fragments of *F. prausnitzii* under conditions which allow cells specific to *F. prausnitzii* to be activated. In the methods of prior art, it was then necessary to measure (for example by flow cytometry) the number of the DP8αTreg which secrete cytokines typically secreted by regulatory T cells, in particular IFN-γ and/or IL-10, after being contacted with APCs loaded with *F. prausnitzii* or fragments of *F. prausnitzii*, in order to determine the percentage of *F. prausnitzii*-induced DP8α Treg.

Method of Diagnosing a Disease Characterized by a Decrease of *F. prau*

In one aspect, the invention relates to a method, particularly an in vitro method, of determining if a subject is afflicted with a disease characterized by a decrease of *F. prausnitzii*, wherein said method comprises:

a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype or a CD4$^+$ CD8αα$^{low}$ CCR6$^+$ CXCR6$^+$ phenotype, in a biological sample from the subject, b) optionally, comparing the result of step (a) with i) a control standard value corresponding to the number and/or concentration and/or proportion of these T lymphocytes typically found in a biological sample of the same nature from a healthy subject, and/or ii) a control standard value corresponding to the number and/or concentration and/or proportion of these T lymphocytes typically found in a biological sample of the same nature from a patient suffering from said disease characterized by a decrease of *F. prausnitzii*; and c) deducting from the result(s) of step (a) and/or step (b) where appropriate, if the subject is afflicted with a disease characterized by a decrease of *F. prausnitzii*.

The disease characterized by a decrease of *F. prausnitzii* is particularly IBD.

In some embodiments, the method comprises a first step consisting of providing or obtaining a biological sample, particularly a blood sample, such as total blood or a blood fraction, from the subject to be diagnosed.

In particular, in this aspect of the invention, the subject to be diagnosed is suspected to be afflicted with a disease characterized by a decrease of *F. prausnitzii*, particularly with an inflammatory bowel disease: thus the method can be performed to confirm that the subject is indeed suffering from a disease characterized by a decrease of *F. prausnitzii*, particularly an inflammatory bowel disease.

In a preferred embodiment, step (a) is carried out with a blood sample, for example total blood or a blood fraction including peripheral blood mononuclear cells (PBMC) and/or peripheral blood lymphocytes (PBL). This embodiment is particularly advantageous because collecting a blood sample is both easier and less invasive than performing colonoscopy and colonic biopsy, the standard tests currently requested for diagnosing for example IBD.

In a preferred embodiment, the number and/or concentration and/or proportion of T lymphocytes with a CD4$^+$ CD8αα$^{low}$ CXCR6$^+$ phenotype, more particularly with a CD4$^+$ CD8αα$^{low}$ CCR6$^+$ CXCR6$^+$ phenotype is/are determined in step a).

The "control standard value" used in step (b) may be obtained by, for example, determining the proportion and/or number and/or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in a biological sample (particularly a blood sample, such as total blood or a blood fraction) of a given population of subjects (e.g. healthy subjects, patients suffering from a disease characterized by a decrease of *F. prausnitzii*, such as IBD, patients in remission of IBD) and obtaining an average or median figure.

As will be clear to the skilled person, the nature of the comparison of the proportion, number and/or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype determined in a subject biological sample to be tested, with the control and the conclusion drawn in step (c) will depend on the nature of the control.

A proportion, number or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in the biological sample of the subject to be tested equal to, similar to or greater than, the corresponding healthy subject control standard value may be indicative that the patient is not afflicted with a disease characterized by a decrease of *F. prausnitzii*, such as IBD.

In contrast, a proportion, number or concentration value of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype lower than the corresponding healthy subject control standard value may be indicative that the patient is afflicted with a disease characterized by a decrease of *F. prausnitzii*, such as IBD.

Similarly, a proportion, number or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype equal to, similar to or lower than, the corresponding control standard value corresponding to the number and/or concentration and/or proportion of these T lymphocytes typically found in a biological sample of the same nature from a patient suffering from a disease characterized by a decrease of *F. prausnitzii*, such as IBD, may be indicative that the patient suffers from said disease.

For example, a proportion of less than 10, particularly less than 9, more particularly less than 8, for example less than 7,875 T lymphocytes with a CD4$^+$ CD8αα$^{low}$ CCR6$^+$ CXCR6$^+$ phenotype per 10000 CD3$^+$ cells may be indicative that the patient is afflicted with a disease characterized by a decrease of *F. prausnitzii*, in particular of IBD.

In a preferred embodiment wherein the disease characterized by a decrease of *F. prausnitzii* is particularly IBD, the method as defined above is a method of determining if a subject is afflicted with IBD or with an infectious colitis. For example, a proportion of less than 10, particularly less than 9, more particularly less than 8, for example less than 7,875 T lymphocytes with a CD4$^+$ CD8αα$^{low}$ CCR6$^+$ CXCR6$^+$ phenotype per 10000 CD3$^+$ cells may be indicative that the patient is afflicted with IBD, whereas a proportion of more than 7,875, particularly more than 8, more particularly more than 9, for example more than 10 T lymphocytes with a CD4$^+$ CD8αα$^{low}$ CCR6$^+$ CXCR6$^+$ phenotype per 10000 CD3$^+$ cells may be indicative that the patient is afflicted with infectious colitis.

Method of Prognosing Patients Afflicted with a Disease Characterized with a Decrease of *F. prau*

The present invention also relates to a method, particularly an in vitro method, of prognosing outcome of a disease characterized by a decrease of *F. prausnitzii* in a patient suffering from said disease, wherein said method comprises or consists of:
  a) a step of determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the patient, and
  b) deducing from the result of step a) the prognosis of said patient.

The disease characterized by a decrease of *F. prausnitzii* is as defined above.

The disease characterized by a decrease of *F. prausnitzii* is particularly IBD.

As regard to step b), the greater the proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, the better the prognosis.

In some embodiments, the method comprises a first step consisting of providing or obtaining a biological sample, particularly a blood sample, from the patient afflicted with a disease characterized by a decrease of *F. prausnitzii*, such as IBD.

In a preferred embodiment, step (a) is carried out with a blood sample, such as total blood or a blood fraction.

In a preferred embodiment, the number and/or concentration and/or proportion of T lymphocytes with a CD4$^+$ CD8αα$^{low}$ CXCR6$^+$ phenotype, more particularly with a CD4$^+$ CD8αα$^{low}$ CCR6$^+$ CXCR6$^+$ phenotype is/are determined in step a).

In a patient afflicted with a disease characterized by a decrease of *F. prausnitzii*, such as IBD, a low level of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype is likely indicative of a poor prognosis. On the contrary, the higher the number of these specific T lymphocytes is, the better the prognosis is.

Hence, the measurement of no or a low number and/or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in step a) is indicative of a poor prognosis, whereas the measurement of high levels of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in step b) is indicative of a good prognosis.

As used throughout the present specification, the term "poor prognosis" refers to a patient who is likely to experience an early relapse and/or to not respond to a new treatment recently initiated. The term "good prognosis" refers to a patient who is likely to have long periods of remission and/or to have a good response to a new treatment recently initiated.

As indicated above, the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype determined in step a) provides an evaluation of the prognosis of the outcome of a disease characterized by a decrease of *F. prausnitzii* in a patient afflicted with this condition. Therefore, in a preferred embodiment of the method of the invention, in order to evaluate the prognosis, the value obtained in step a) is applied to a standard calibration curve showing a relationship between the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in the biological sample and the probable outcome (relapse, short or long period of remission, progression to a severe form of the disease . . . ).

The standard calibration curve can be obtained by determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in a large cohort of patients whose outcome is known.

The method as defined above of prognosing outcome of a disease characterized by a decrease of *F. prausnitzii* in a patient suffering from said disease for example comprises or consists of:
  a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the patient,
  a') optionally, comparing the result of step a) with a standard calibration curve showing a relationship between the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in a biological sample and the probable outcome, and
  b) deducing from the result(s) of step a) and/or a') where appropriate, the prognosis of said patient.

In one embodiment, the biological sample is obtained prior to the patient receiving any therapy.

In another embodiment, the biological sample is obtained after initiation of a treatment of a disease characterized by a decrease of *F. prausnitzii*, in particular after initiation of a treatment according to the invention as disclosed below.

Method of Predicting the Risk of Developing a Disease Characterized with a Decrease of *F. prau*

The inventors have shown that the level of T regulatory lymphocytes with a CD4$^+$ CD8αα$^{low}$ phenotype which are specific for *F. prausnitzii* in a patient, in particular in patient's blood and patient's colonic mucosa, is associated with the intestinal immunologic homeostasis and with the development of inflammatory bowel diseases.

Therefore, the present invention relates to a method, particularly an in vitro method, of predicting whether a subject is at risk of developing a disease characterized by a decrease of *F. prausnitzii* or a disease associated with a decrease of *F. prausnitzii*, wherein said method comprises or consists of:
  a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype or a CD4$^+$ CD8αα$^{low}$ CCR6$^+$ CXCR6$^+$ phenotype, in a biological sample from the subject;
  b) predicting from the result of step a) if the subject is at risk of suffering from a disease characterized by or associated with a decrease of *F. prausnitzii*, in particular wherein a low value at step a) relative to a reference value for a sample of the same nature, indicates that said subject is at risk of developing a disease characterized by or associated with a decrease of *F. prausnitzii*.

The method as defined above of predicting whether a subject is at risk of developing a disease characterized by or associated with a decrease of *F. prausnitzii* for example comprises or consists of:
- a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype or a CD4$^+$ CD8αα$^{low}$ CCR6$^+$ CXCR6$^+$ phenotype, in a biological sample from the subject;
- a') optionally, comparing the result of step a) with a reference value for a sample of the same nature,
- b) predicting from the result(s) of step a) and/or a') where appropriate, if the subject is at risk of suffering from a disease characterized by or associated with a decrease of *F. prausnitzii*.

The disease characterized by a decrease of *F. prausnitzii* is particularly IBD.

The disease associated with a decrease of *F. prausnitzii* is particularly GvHD.

In some embodiments, the method comprises a first step consisting of providing or obtaining a biological sample, particularly a blood sample, from the subject to be tested.

In a preferred embodiment, step a) is carried out with a blood sample, such as total blood or a blood fraction.

The subject to be tested is not yet afflicted with a disease characterized by a decrease of *F. prausnitzii*. For example, when the method is a method of predicting whether a subject is at risk of developing IBD, the subject to be tested is not yet afflicted with IBD.

The method as defined above of predicting whether a subject is at risk of developing GvHD is particularly useful before performing any transplant in said subject.

In a preferred embodiment, the number and/or concentration and/or proportion of T lymphocytes with a CD4$^+$ CD8αα$^{low}$ CXCR6$^+$ phenotype, more particularly with a CD4$^+$ CD8αα$^{low}$ CCR6$^+$ CXCR6$^+$ phenotype is/are determined in step a).

In an embodiment, the reference value (number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype or a CD4$^+$ CD8αα$^{low}$ CCR6$^+$ CXCR6$^+$ phenotype) is the value determined in a biological sample from a subject who is not afflicted with the disease characterized by a decrease of *F. prausnitzii* and/or with a disease associated with a decrease of *F. prausnitzii*, said biological sample being of the same nature than that of the subject to be tested. The lower the value determined in step (a), the higher the risk of developing the disease characterized by a decrease of *F. prausnitzii* in the future.

In one embodiment, a proportion of less than 10, particularly less than 9, more particularly less than 8, for example less than 7,875 T lymphocytes with a CD4$^+$ CD8αα$^{low}$ CCR6$^+$ CXCR6$^+$ phenotype per 10000 CD3$^+$ cells is indicative that the patient is at risk of developing a disease characterized by a decrease of *F. prausnitzii*, in particular at risk of developing IBD.

Method for the Stratification of a Subject Suffering from or at Risk of Developing a Disease Potentially Associated with a Decrease of *F. prausnitzii*

The present invention thus also relates to a method for the stratification of a subject suffering from or at risk of developing a disease potentially associated with a decrease of *F. prausnitzii* into a category of subjects with a decrease of *F. prausnitzi* or a category of subjects with standard level of *F. prausnitzii*, wherein said method comprises:
- a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the subject,
- b) optionally, comparing the result of step a) with i) a control standard value corresponding to the number and/or concentration and/or proportion of these T lymphocytes typically found in a biological sample of the same nature from a healthy subject, and/or ii) a control standard value corresponding to the number and/or concentration and/or proportion of these T lymphocytes typically found in a biological sample of the same nature from a patient suffering from said disease characterized by a decrease of *F. prausnitzii*; and
- c) from the result(s) of step a) and/or step b) where appropriate, stratifying the subject into a category of subjects with a decrease of *F. prausnitzi* or a category of subjects with standard level of *F. prausnitzii*.

The disease potentially associated with a decrease of *F. prausnitzii* is as defined above.

Said disease potentially associated with a decrease of *F. prausnitzii* may for example be selected from the group consisting of an allergy, a cancer, particularly colon cancer, obesity, Graft Versus Host Disease, a disease wherein the decrease of *F. prausnitzii* results from a treatment and their combinations.

The disease wherein the decrease of *F. prausnitzii* results from a treatment may for example result from and antibiotic treatment and/or a chemotherapy.

Some patients receiving a treatment, such as an antibiotic treatment and/or a chemotherapy, indeed do not recover after the end of said treatment the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype they had before treatment.

The subject suffering from or at risk of developing a disease potentially associated with a decrease of *F. prausnitzii* is for example a subject having received a treatment that may result in a decrease of *F. prausnitzii*, a subject suffering from or at risk of developing allergy, a subject suffering from or at risk of developing obesity, a subject suffering from or at risk of developing GvHD and/or a subject suffering from or at risk of developing cancer, for example colon cancer.

In some embodiments, the method comprises a first step consisting of providing or obtaining a biological sample, particularly a blood sample, such as total blood or a blood fraction, from the subject.

In a preferred embodiment, step (a) is carried out with a blood sample, for example total blood or a blood fraction including peripheral blood mononuclear cells (PBMC) and/or peripheral blood lymphocytes (PBL).

In a preferred embodiment, the number and/or concentration and/or proportion of T lymphocytes with a CD4$^+$ CD8αα$^{low}$ CXCR6$^+$ phenotype, more particularly with a CD4$^+$ CD8αα$^{low}$ CCR6$^+$ CXCR6$^+$ phenotype is/are determined in step a).

The "control standard value" used in step (b) may be obtained by, for example, determining the proportion and/or number and/or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in a biological sample (particularly a blood sample, such as total blood or a blood fraction) of a given population of subjects (e.g. healthy subjects, patients suffering from a disease potentially associated with a decrease of *F. prausnitzii* and with standard levels of *F. prausnitzii*, patients suffering from a disease potentially associated with a decrease of *F. prausnitzii* and having a decrease of *F. prausnitzii*, patients having received a treatment which may result in a decrease of *F. prau* snitziiand having standard levels of *F. prausnitzii*, or patients having received a treatment which may result in a decrease of *F. prausnitzii* and having a decrease of *F. prausnitzii*) and obtaining an average or median figure.

As will be clear to the skilled person, the nature of the comparison of the proportion, number and/or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype determined in a subject biological sample to be tested, with the control and the conclusion drawn in step (c) will depend on the nature of the control.

A proportion, number or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in the biological sample of the subject to be tested equal to, similar to or greater than, the corresponding healthy subject control standard value may be indicative that the patient belongs to the category of subjects with standard level of *F. prausnitzii*.

In contrast, a proportion, number or concentration value of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype lower than the corresponding healthy subject control standard value may be indicative that the patient belongs to the category of subjects with a decreased level of *F. prausnitzii*.

Similarly, a proportion, number or concentration of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype equal to, similar to or lower than, the corresponding control standard value corresponding to the number and/or concentration and/or proportion of these T lymphocytes typically found in a biological sample of the same nature from a patient suffering from said disease potentially associated with a decrease of *F. prausnitzii* and having indeed a decrease of *F. prausnitzii* may be indicative that the patient belongs to the category of subjects with a decrease of *F. prausnitzi*.

For example, a proportion of less than 20, particularly less than 15, more particularly less than 10, for example less than 9 T lymphocytes with a CD4$^+$ CD8αα$^{low}$ CCR6$^+$ CXCR6$^+$ phenotype per 10000 CD3$^+$ cells is indicative that the patient belongs to the category of subjects with a decrease of *F. prausnitzi* and/or a proportion of more than 9, particularly more than 10, more particularly more than 15, for example more than 20 T lymphocytes with a CD4$^+$ CD8αα$^{low}$ CCR6$^+$ CXCR6$^+$ phenotype per 10000 CD3$^+$ cells is indicative that the patient belongs to the category of subjects with standard level of *F. prausnitzii*.

When the patient belongs to the category of subjects with a decrease of *F. prau*, said patient thus suffers or is likely to suffer from a disease associated with a decrease of *F. prausnitzi*.

If the subject is stratified into a category of subjects with a decrease of *F. prausnitzii*, the method may further comprise a step of administering to said subject isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype or a pharmaceutical composition comprising thereof.

If the subject is stratified into a category of subjects with a decrease of *F. prausnitzii*, the method may further comprise a method of monitoring the efficacy of a preventive or curative treatment of said disease.

Isolated T Lymphocytes with a CD4$^+$ CD8αα$^{low}$ CCR6+ Phenotype, a CD4$^+$ CD8αα$^{low}$ CXCR6+ Phenotype and/or a CD4$^+$ CD8αα$^{low}$ CCR6+ CXCR6+ Phenotype The present invention also relates to isolated T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype, i.e. a population of said isolated T lymphocytes.

Upon activation, these T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype particularly secrete IL-10 and/or do not secrete IL-17 and TGFB.

These T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype particularly express CD38, CD39, CD73 and RORY and, particularly, do not express CD62L.

These isolated T lymphocytes are particularly primary culture cells or cells from an established cell line or from a clone, said established cell line or clone being particularly derived from primary culture cells.

The isolated T lymphocytes may be isolated from a biological sample. Said biological sample is as defined above, particularly a blood sample, such as total blood or blood fraction.

Isolating T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype can be carried out by using positive and, optionally, negative selection according to the surface proteins which are, or which are not, expressed by the these lymphocytes. Methods of isolating/selecting cells based on the presence or the absence of cell surface proteins are well-known to one skilled in the art. For instance, these cells may be isolated/purified by immunologic selection/immunosorting using antibodies which selectively bind to a selected cell surface protein.

Isolation/purification of T lymphocytes with a CD4$^+$ CD8αα$^{low}$ CCR6+ phenotype, a CD4$^+$ CD8αα$^{low}$ CXCR6$^+$ phenotype and/or a CD4$^+$ CD8αα$^{low}$ CCR6+ CXCR6+ phenotype may be carried out by the method as defined above for selecting T regulatory lymphocytes with a CD4$^+$ CD8αα$^{low}$ phenotype which are specific for *F. prausnitzii*.

Primary culture cells are cells isolated directly from living tissue, particularly a blood sample. These cells have undergone very few population doublings following their isolation.

Methods of generating cell lines derived from primary culture cells are known to the person having ordinary skill in the art, and includes in particular the methods described by Gregori et al. (*Methods Mol Biol.*, 677: 31-46, 2011). For instance, T cell lines can be generated by stimulations with PHA, irradiated feeder cells and IL-2, as described by Fonteneau et al. (*J Immunol* 159, 2831-2839, 1997).

In particular, the isolated T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype were previously activated and/or expanded.

Activation and/or expansion (also called "proliferation") of the T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype can be performed by contacting these T lymphocytes with APCs loaded with *F. prausnitzii* or fragments of *F. prausnitzii* under conditions which allow cells specific to *F. prausnitzii* to be activated. Activation may be assessed by determining if the isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype (in particular, cells line or primary cells) express cytokines typically secreted by regulatory T cells, in particular TNF-α, IFN-γ and/or IL-10.

The APCs can be professional or non-professional APCs. In particular, the APCs are professional APCs. More particularly, APCs are chosen from the group consisting of Dendritic cells, Macrophages or Monocytes.

Proliferation of T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6$^+$ CXCR6$^+$ phenotype can also be triggered ex vivo (or in vitro) upon CD3 activation and/or CD28 activation (e.g. proliferation can be induced by using an antibody directed against these surface proteins).

In particular, the population of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype is isolated from a subject to be treated, more particularly from a blood sample.

The isolated T lymphocytes are particularly T lymphocytes with a CD4$^+$ CD8αα$^{low}$ CXCR6$^+$ phenotype, more particularly a CD4$^+$ CD8αα$^{low}$ CCR6$^+$ CXCR6$^+$ phenotype.

In the context of the invention, the T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype are particularly formulated into a pharmaceutical composition, particularly in an effective amount (i.e. an amount which is capable of preventing and/or treating the disease characterized by a decrease of *F. prau*, without causing overly negative effects in the administered subject).

The pharmaceutical composition is particularly suitable for an administration by the intravenous route or arterial route.

Methods of Treating and/or Preventing a Disease Characterized by a Decrease of *F. prau*

The invention also relates to a method of treating and/or preventing a disease characterized by a decrease of *F. prausnitzii* in a patient in need thereof or a disease associated with a decrease in *F. prausnitzii* in a patient need thereof, comprising or consisting of a step of administering to said patient a therapeutically effective amount of isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$.

The present invention also relates to isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$, particularly a population of said isolated T lymphocytes, for use as a medicament in a method for preventing and/or treating a disease characterized by a decrease of *F. prausnitzii*, in particular in a subject in need thereof, and/or in a method for treating a disease potentially associated with a decrease in *F. prau* in a patient having a decrease of *F. prau*.

The disease characterized by a decrease of *F. prausnitzii* is as defined above, more particularly IBD and/or colon cancer.

As mentioned above, a disease associated with a decrease in *F. prau* means that said disease is potentially associated with a decrease in *F. prau* and that said patient belongs to the category of patients with a decrease of *F. prau*.

The disease potentially associated with a decrease of *F. prausnitzii* is as defined above, more particularly allergy, obesity, Graft Versus Host Disease, a disease wherein the decrease of *F. prausnitzii* results from a treatment and/or colon cancer.

The subject in need thereof may for example be a subject having received a treatment which resulted in a decrease of *F. prau*, a subject suffering from or at risk of developing allergy, a subject suffering from or at risk of developing obesity, a subject suffering from or at risk of developing GvHD a subject suffering from or at risk of developing cancer, for example colon cancer, and/or a subject suffering from or at risk of developing IBD.

In the case of a disease associated with a decrease in *F. prau*, the above uses and methods particularly allows improving the prevention and/or treatment with at least one drug, which is usually used or administered for the prevention and/or treatment of said disease. Thus, in the case of a disease associated with a decrease in *F. prau*, the isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ are particularly used or administered in combination with at least one other drug used or administered for the prevention and/or treatment of said disease.

The isolated T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ are as defined above in the section of the same name.

The isolated T lymphocytes are preferable with a CD4$^+$ CD8αα$^{low}$ CXCR6$^+$ phenotype, more particularly with a CD4$^+$ CD8αα$^{low}$ CCR6$^+$ CXCR6$^+$ phenotype.

The T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ are particularly provided in the form of a pharmaceutical composition, for example as defined above.

The dosage of T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype required to in the subject to be treated can vary according to numerous factors, the presence and the nature of co-stimulatory molecules (e.g. cytokines . . . ), the mode of administration, the age, weight, condition of the subject, the route of administration, the frequency of administration, the other ingredients in the pharmaceutical composition, and the severity of the disease. Generally, the T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype for use in the prevention and/or treatment of a disease characterized by a decrease of *F. prau* and/or of a disease associated with a decrease in *F. prau* may be administered in the range from about $10^5$ cells/kg to about $10^8$ cells/kg, alternatively from about $10^7$ cells/kg to about 108 cells/kg or from about $0.1 \times 10^6$ cells/kg to $5 \times 10^6$ cells/kg of the patient.

The isolated T lymphocytes with a CD4+ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ may be used or administered by intravenous route or arterial route. In some embodiments, the administration can be given at multiple locations.

In particular, the T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype or the pharmaceutical composition comprising these T lymphocytes, are administered intravenously.

In particular, the isolated T lymphocytes with a CD4+ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$, used to carry out the above uses and methods, are isolated from blood (for example peripheral blood lymphocytes and/or PBMC).

The T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ are particularly isolated by the method for selecting T regulatory lymphocytes with a CD4$^+$ CD8αα$^{low}$ phenotype which are specific for *F. prausnitzii* as defined above.

The T lymphocytes with a CD4+ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ may be primary culture cells or cells from an established cell line or from a clone, said established cell line or clone being particularly derived from primary culture cells.

By the expression "established cell line", it is herein meant a cell line whose cells can be cultured indefinitely in vitro.

In a preferred embodiment, the isolated population of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ are obtained from the subject to be treated (i.e. are autologous lymphocytes). Use of autologous lymphocytes is particularly advantageous since rejection of the administered lymphocytes by the recipient is avoided.

The present invention also relates to a method of treating and/or preventing a disease characterized by a decrease of *F. prausnitzii* in a patient in need thereof, wherein said method comprises or consists of the following steps:
(i) isolating a population of T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype, particularly from said patient;
(i') optionally, generating a cell line or clone from said isolated population of step (i);
(ii) activating and/or expanding said isolated population of step (i) or the cells lines of step (i') where appropriate, by culturing these cells in a culture medium comprising:
a compound suitable for activating CD3 and/or CD28 pathway(s) (e.g. anti-CD3 anti-CD28 antibodies, phorbolmyristate acetate and/or calcium ionophore); and/or
APCs loaded with *F. prausnitzii* or fragments of *F. prausnitzii*;
(iii) administering the activated and/or expanded of T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+ phenotype of step (ii) to the patient in a therapeutically effective amount.

Method of Monitoring the Efficacy of a Treatment of an Inflammatory Bowel Disease The invention further provides a method of monitoring the efficacy of a preventive or curative treatment of a disease characterized by or associated with a decrease of *F. prausnitzii*, the method comprises a step of monitoring the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype, in a biological sample from the subject during the treatment.

The disease characterized by a decrease of *F. prausnitzii* is particularly IBD.

The disease associated with a decrease of *F. prausnitzii* is as defined above.

In a preferred embodiment, the number and/or concentration and/or proportion of T lymphocytes with a CD4$^+$ CD8αα$^{low}$ CXCR6$^+$ phenotype, more particularly with a CD4$^+$ CD8αα$^{low}$ CCR6$^+$ CXCR6$^+$ phenotype is/are monitored.

An increase in the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype over the course of the treatment may indicate that the treatment is effective.

A decreased or a stable number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype over the course of the treatment may indicate that the treatment is not or not any more effective.

The method as defined above of monitoring the efficacy of a preventive or curative treatment of a disease characterized by or associated with a decrease of *F. prausnitzii* for example comprises:
a) determining the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in a biological sample from the subject during the treatment,
b) comparing the result of step a) with the number and/or concentration and/or proportion of T lymphocytes with a CD4$^+$ CD8αα$^{low}$ CCR6$^+$ phenotype, a CD4$^+$ CD8αα$^{low}$ CXCR6$^+$ phenotype and/or a CD4$^+$ CD8αα$^{low}$ CCR6$^+$ CXCR6$^+$ phenotype in a biological sample from said subject at an earlier time during treatment,
c) deducing from the result of step b) if the treatment is effective.

Particularly, the treatment comprises, or consists in administering immunosuppressant (notably azathioprine, 6-mercaptopurine, methotrexate, tacrolimus, ciclosporin), biologics (notably monoclonal antibodies including anti-TNFalpha), probiotics, (i.e. live microorganisms that may confer a health benefit on the host) or antibiotics.

Alternatively, the treatment may comprise or consist in, administering *F. prausnitzii* (a live, live-attenuated and/or killed *F. prausnitzii* strain) or a fragment of *F. prausnitzii*. Particularly, the probiotics, the *F. prausnitzii* or fragment thereof are formulated into a pharmaceutical composition.

Particularly, the biological sample is a blood sample, such as total blood or a blood fraction, including peripheral blood mononuclear cells (PBMC) and/or peripheral blood lymphocytes (PBL).

Kits

The invention also provides kits that are useful in the above methods and uses of the invention.

The present invention thus relates to a kit, particularly for diagnosing, prognosing and/or predicting the risk of developing a disease characterized by a decrease of *F. prausnitzii*, and/or for monitoring the efficacy of a treatment of a disease characterized by a decrease of *F. prausnitzii* and/or for selecting T regulatory lymphocytes with a CD4+ CD8αα$^{low}$ phenotype which are specific for *F. prausnitzii*, wherein said kit comprises means for determining the number and/or concentration and/or proportion of T lymphocytes with a CD4$^+$ CD8αα$^{low}$ CCR6+ phenotype, a CD4$^+$ CD8αα$^{low}$ CXCR6+ phenotype and/or a CD4$^+$ CD8αα$^{low}$ CCR6+ CXCR6+.

In a preferred embodiment, the kit as defined above comprises:
- at least one antibody or fragment thereof specific for CCR6 and/or at least one antibody specific for CXCR6,
- at least one antibody or fragment thereof specific for CD4,
- at least one antibody or fragment thereof specific for CD8α, and
- optionally, at least one antibody of fragment thereof specific for CD3.

The antibodies or fragments thereof specific for CCR6, CXCR6, CD4, CD3 and CD8a particularly allow a positive selection of the cells based on the presence of these proteins.

The kit particularly does not comprise any antibody or fragment thereof specific for Foxp3.

The antibodies used in the kit are particularly labeled with a detectable compound, such as a fluorophore or radioactive compound. Alternatively, the kit may further comprise secondary antibody(ies), labeled with a detectable compound, which binds to an unlabelled antibody (also called primary antibody).

According to an embodiment, the kit comprises, in addition to the means for determining the number and/or concentration and/or proportion of T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype and/or a $CD4^+$ $CD8\alpha\alpha^{low}$ $CCR6^+$ $CXCR6^+$, one or more control samples ("control standard value") comprising a known number and/or concentration and/or proportion of T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype and/or a $CD4^+$ $CD8\alpha\alpha^{low}$ $CCR6^+$ $CXCR6^+$, said number and/or concentration and/or proportion being representative of a given population of subjects (e.g healthy subjects, patients suffering from a disease characterized by a decrease of F. prau, patients in remission, patient at risk of developing said disease).

Further, the kit can comprise instructions for the use of said kit i) in predicting whether a subject is at risk of developing a disease characterized by a decrease of F. prau, such as IBD and/or colon cancer, and/or ii) in diagnosing a disease characterized by a decrease of F. prau, such as an IBD and/or iii) in prognosing a disease characterized by a decrease of F. prau, such as an IBD.

The kit can also comprise a standard calibration curve showing a relationship between the number and/or concentration and/or proportion of T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype and/or a $CD4^+$ $CD8\alpha\alpha^{low}$ $CCR6^+$ $CXCR6^+$ in the biological sample and the probable outcome of the disease (relapse, short or long period of remission, progression to a severe form of the disease . . . ).

The standard calibration curve can be obtained by determining the number and/or the concentration and/or proportion of T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype and/or a $CD4^+$ $CD8\alpha\alpha^{low}$ $CCR6^+$ $CXCR6^+$ in a large cohort of patients whose outcome is known.

The invention further relates to a kit for treating or preventing a disease characterized with a decrease of F. prau comprising or consisting of:
- optionally, a packaging material;
- a known amount of a population of isolated lymphocytes with a $CD4^+$ $CD8\alpha\alpha^{low}$ $CCR6^+$ phenotype, a $CD4^+$ $CD8\alpha\alpha^{low}$ $CXCR6^+$ phenotype and/or a $CD4^+$ $CD8\alpha\alpha^{low}$ $CCR6^+$ $CXCR6^+$ or a pharmaceutical composition thereof; and
- optionally, a label or package insert contained with said packaging material indicating that the drug (i.e. said population of isolated lymphocytes) or pharmaceutical composition thereof is effective in the prevention and/or treatment of a disease characterized with a decrease in F. prau, in a subject suffering from a disease characterized with a decrease in F. prau or at risk of developing a disease characterized with a decrease in F. prau.

The disease characterized with a decrease of F. prau is particularly as defined above.

In a particular embodiment, the article of manufacture as described herein comprises a label or package insert further indicating the list of contraindications for the treatment with said drug.

In particular, the population of isolated T lymphocytes with a $CD4^+$ $CD8\alpha\alpha^{low}$ $CCR6^+$ phenotype, a $CD4^+$ $CD8\alpha\alpha^{low}$ $CXCR6^+$ phenotype and/or a $CD4^+$ $CD8\alpha\alpha^{low}$ $CCR6^+$ $CXCR6^+$ is an activated population.

All references cited herein, including journal articles or abstracts, published patent applications, issued patents or any other references, are entirely incorporated by reference herein, including all data, tables, figures and text presented in the cited references.

The invention will be further illustrated by the following figure and examples. However, these examples and figure should not be interpreted in any way as limiting the scope of the present invention.

BRIEF DESCRIPTION OF THE SEQUENCES

Sequence SEQ ID NO: 1 corresponds to the human CCR6 protein of reference AAB57794.1 in GenBank database, as available on Jul. 31, 2017.

Sequence SEQ ID NO: 2 corresponds to the human CXCR6 protein of reference NP_006555.1 in the NCBI database, as available on Jul. 31, 2017.

BRIEF DESCRIPTION OF THE FIGURES

FIG. 7: The frequency of $CCR6^+/CXCR6^+$ DP8α cells within $CD3^+$ T cells was determined and plotted for 10,000 $CD3^+$ cells. A diagnostic threshold was positioned at 7.875 $CCR6^+/CXCR6^+$ DP8α cells per 10,000 $CD3^+$ cells using GraphPad Prism version 6.0.

FIG. 8: The frequency of $CD4^+$ cells within $CD3^+$ T cells was also determined. A One-way ANOVA was used. error bars: sem; **: $p \leq 0.0001$, *: $p=0.001$, **: $p=0.01$.

EXAMPLE

Figure 1:
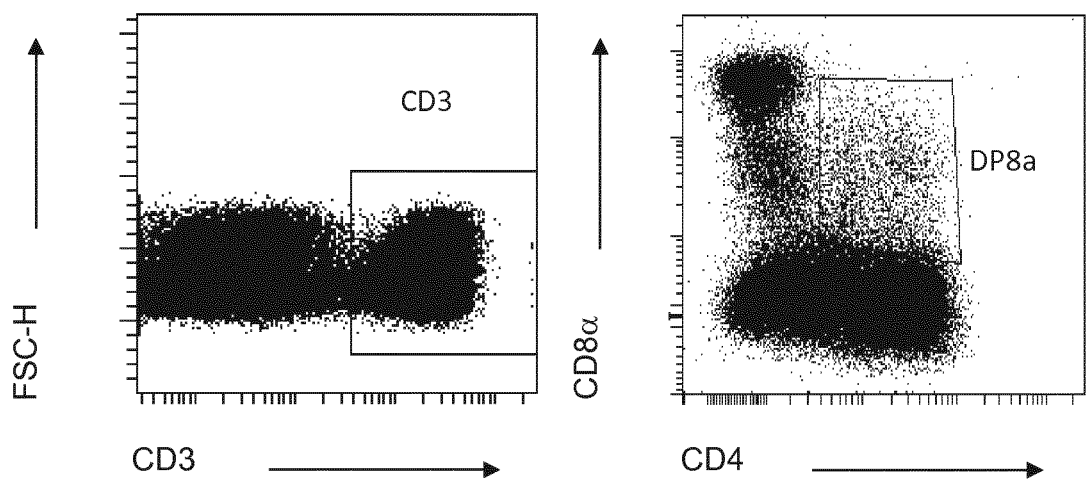
FIG. 1: Colonic lamina propria DP8a T cells express high levels of CCR6, CXCR3 and CXCR6. A. Gating strategy for the detection of CCR6-, CXCR3- and CXCR6-expressing DP8a cells. Colonic lamina propria were dissociated as described in Methods. A representative example is shown. B. The frequency for each subset is represented as a mean of 5 donors.
Figure 1:
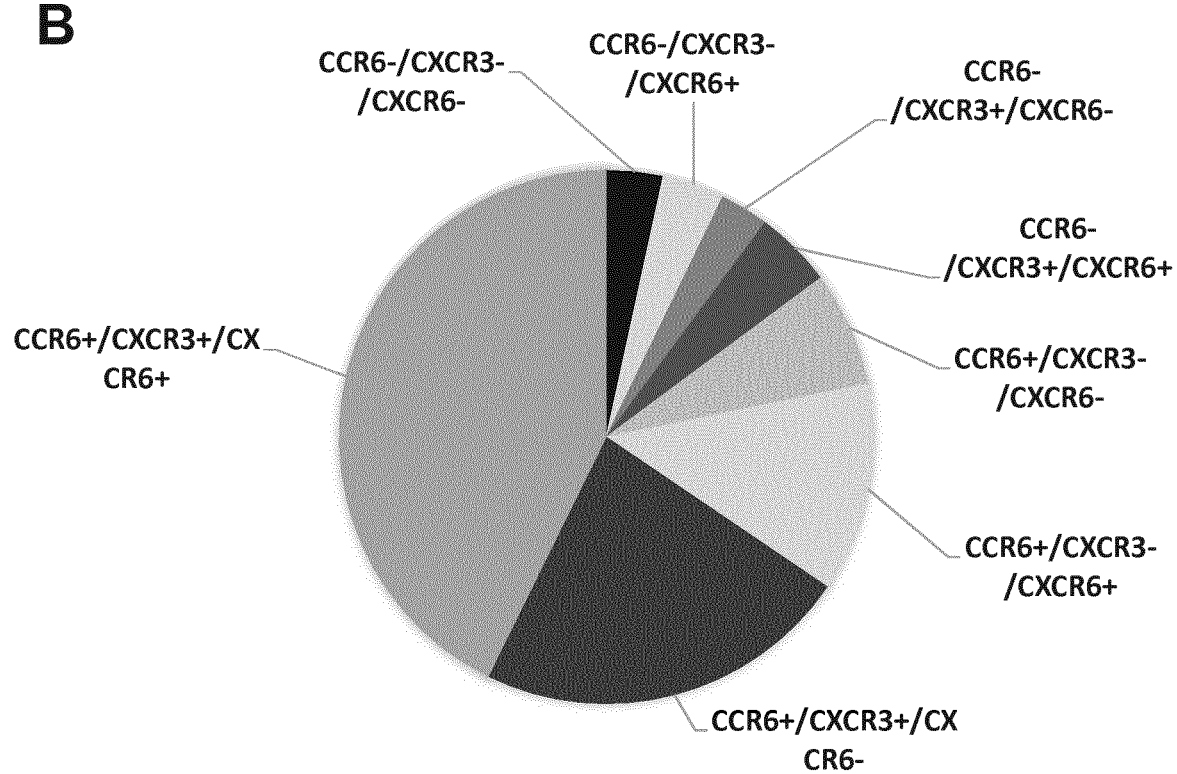

Example 1: $CCR6^+/CXCR6^+$ DP8a T Cells and IBD

Material and Methods
(i) Reagents

Human Peripheral blood mononuclear cells (PBMCs), purified monocytes or lymphocytes were cultured in RPMI-1640 supplemented with 5% human Serum, 2 mM L-glutamine and 10 μg/ml penicillin-streptomycin (Gibco). rhIL-2 was used for the culture and expansion of T cells. Violet Proliferation Dye 450 (VPD) (1 μM, BD Bioscience), anti-CD3/anti-CD28 activation beads (Gibco), Brefeldin A (10 mg/ml, Sigma-Aldrich), and 4% paraformaldehyde (Sigma-Aldrich) were used.

(ii) Bacterial Cultures

F. prausnitzii A2-165 were obtained from Commensal and Probiotic-Host Interactions Laboratory, UMR1319 Micalis, INRA, Jouy-en-josas, France. F. prausnitzii was grown for 20 h at 37° C. in LYBHI medium (brain-heart infusion medium supplemented with 0.5% yeast extract; Difco), cellobiose (1 mg/ml; Sigma-Aldrich), maltose (1 mg/ml; Sigma-Aldrich), and cysteine (0.5 mg/ml; Sigma-Aldrich) in an anaerobic chamber. F. prausnitzii was used after sonication.

(iii) Cell Separation

PBMCs were isolated by Ficoll gradient centrifugation from healthy donor blood (EFS, Nantes, France), IBD patients or infectious colitis patients. This latter study was approved by the ethics committee of the Comité de Protection des Personnes Ile-de-France IV (Suivithèque). Several patients also came from the CHU of Nantes hospital. All patients signed informed consent forms. Patients' and donors' characteristics are shown in supplementary Table I.

Monocytes and CD4 T cells were purified using CD14 and CD4 microbeads, respectively, according to the supplier's instructions (Miltenyi).

Normal colonic mucosa was obtained from colorectal cancer patients from surgically resected tissue, taken approximately 10 cm downstream of the tumor. The lamina propria was separated from the epithelium after incubation in 1 mM EDTA PBS buffer (20 min) and then minced into approximatively 1 $mm^2$ fragments and washed with RPMI containing penicillin (10%) and gentamycin (0.1 mg/ml; Sigma-Aldrich). Tissue fragments were digested with collagenase IV (1 mg/ml; Sigma-Aldrich), with shaking at 37° C. Mucus and large debris were removed by filtration through a 40 mm-cell strainer (BD). Viable cells were obtained by Ficoll gradient centrifugation. Cells were then cultured for 7 days in RPMI with 10% FBS, 2× antibiotics, 1× fungizone and 150 UI/ml IL-2, before stainings were performed. During this time, some samples got infected and were discarded. Uninfected samples recovered from collagenase-treatment and re-expressed markers which were then studied. This study was approved by the ethics committee of the CHU de Nantes. All patients signed informed consent forms.

(iv) Antibodies

For surface staining, cells were harvested, washed and stained for 30 min at 4° C. in PBS 0.1% BSA with the following Abs: anti CD3-PECy7 (clone UCHT1, Becton Dickinson), anti CD4-FITC (clone 13B8.2, Beckman Coulter), anti CD8a-APC (clone B9.11, Beckman Coulter), –BV605 (clone SK1, Becton Dickinson) or -BV421 (clone RPA-T8, Becton Dickinson) CCR6-BV421 (clone 11A9, Becton Dickinson) or -PE (clone G034E3, Biolegend), CXCR3-BV785 (clone G025H7, Biolegend), CXCR6-APC (clone K041E5, Biolegend), anti β7-PE (clone FIB504, Becton Dickinson), For intracellular staining, cells were harvested, fixed in 4% paraformaldehyde, washed and stained for 30 min at RT in PBS 0.1% BSA 0.1% saponin with anti-IFNg-APC (clone B27, Becton Dickinson).

Fluorescence was measured on FACS LSR II flow cytometer and analyzed using Diva software (Becton Dickinson).

(v) T Cell Culture and Stimulation

Purified CD4+ T cells or PBLs were stained with violet proliferation dye (VPD) and stimulated by autologous monocytes (ratio 10 lymphocytes:1 monocyte) loaded ON or not with bacteria (10 bacteria:1 monocyte). As a positive control, T cells were stimulated by CD3/CD28 beads (3 T cells:1 bead). VPD dilution was assessed 5 days later.

To obtain *F. prau*-specific T cell clones, VPD-stained CD4+ T cells were stimulated as above. At day 5, VPD$^{low}$ DP8α T cells were sorted and cloned using a FACS Aria and amplified using irradiated allogeneic PBMCs and LAZ cells (B-EBV cell line), in the presence of 1 mg/ml PHA and 150 IU/ml rhIL-2.

T cell clones were stimulated by autologous monocytes (ratio 2-3 lymphocytes:1 monocyte) loaded ON or not with bacteria (10 bacteria:1 monocyte). For IFNg detection, T cell clones were stimulated for 6h in the presence of 10 mg/ml brefeldin A before intracellular staining of cytokines. For IL-10 detection, clones were stimulated 48 h by 1 mg/ml coated anti-CD3 (OKT3), before IL-10 measurement by ELISA.

(vi) ELISA

DP8a T cell clones were stimulated or not using coated anti-CD3 (clone OKT3, 1 mg/ml, eBioscience) for 48 h at 37° C. Supernatants were harvested and tested for their IL-10 content using the Ready-Set-Go ELISA according to the manufacturer's guidelines (eBioscience).

(vii) Statistical Analysis

Statistical analysis was performed using GraphPad Prism version 6.0. Most comparisons were performed using 2-sided t-test or one-way ANOVA, as indicated in figure legends. $p<0.05$ was considered statistically significant.

Results

Colonic Lamina Propria DP8a T Cells Express High Levels of CCR6, CXCR3, CXCR6 and b7 Integrin.

To study DP8a T cells within colonic lamina propria lymphocytes (LPLs) for the expression of intestine homing markers, LPL were dissociated using collagenase IV, from 5 human colon tissue resections. Filtered cells were ficolled and cultured as described in the Methods section. It was then stained the CD3+ DP8a cells for CCR6, CXCR3 and CXCR6 at day 7 because the collagenase enzyme temporarily stripped most surface markers from the cell surface (see FIG. 1A et B). As a mean, 78% of LPL-derived DP8a cells expressed CCR6 (composed of CCR6+/CXCR3−/CXCR6−, CCR6+/CXCR3+/CXCR6−, CCR6+/CXCR3−/CXCR6+ and CCR6+/CXCR3+/CXCR6+ DP8α cells), 66% expressed CXCR6 (composed of CCR6−/CXCR3−/CXCR6+, CCR6−/CXCR3+/CXCR6+, CCR6+/CXCR3−/CXCR6+ and CCR6+/CXCR3+/CXCR6+ DP8α cells) and 76% expressed CXCR3 (composed of CCR6−/CXCR3+/CXCR6−, CCR6+/CXCR3+/CXCR6−, CCR6−/CXCR3+/CXCR6+ and CCR6+/CXCR3+/CXCR6+ DP8α cells), among which 50% expressed the 3 markers. Interestingly, most LPL-derived DP8a cells (>57%) co-expressed CCR6 and CXCR6. The majority of LPL-derived DP8a cells also expressed the β7 integrin (data not shown).

Figure 2:
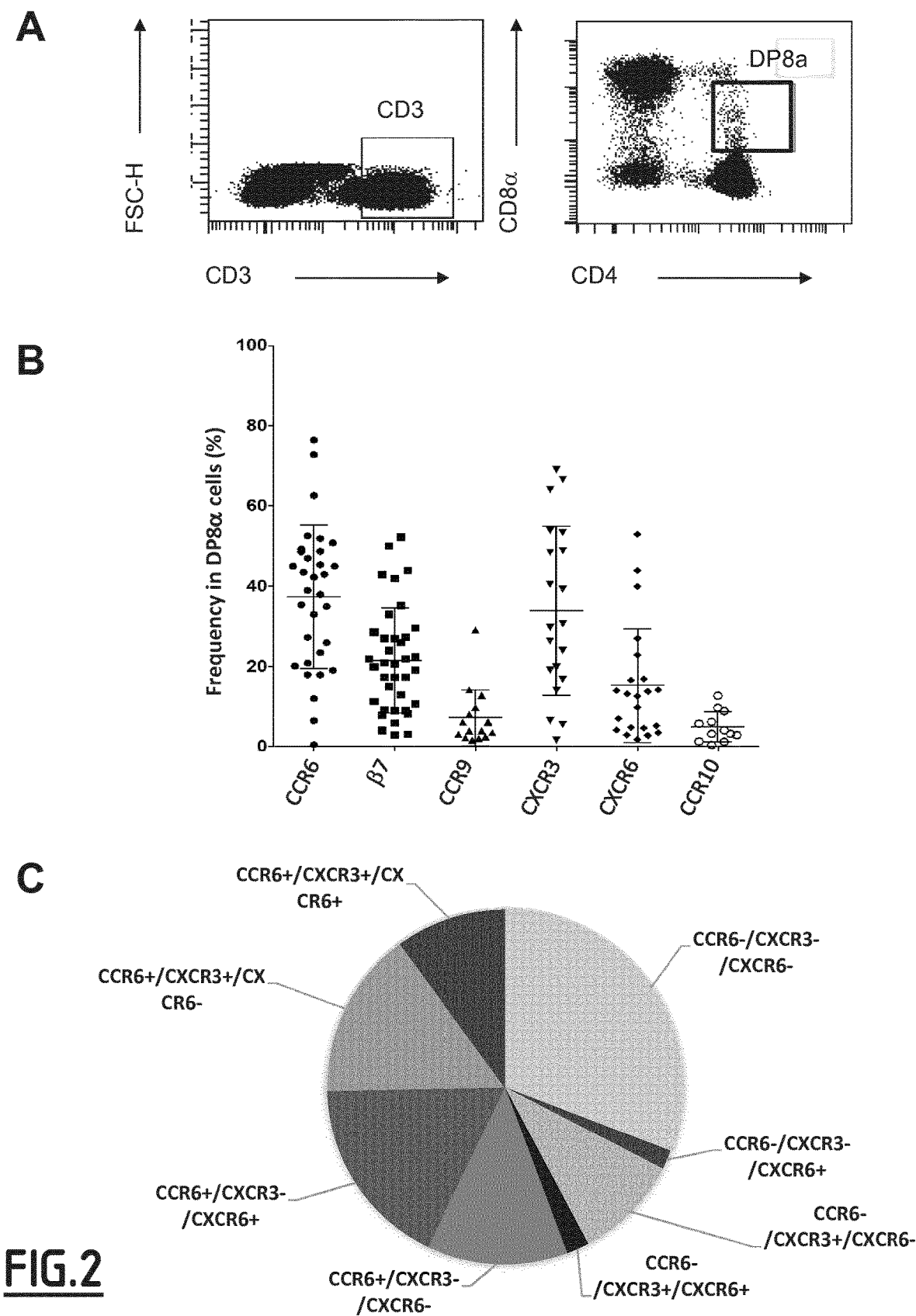
FIG. 2: DP8a T cells circulate in blood and express CCR6, CXCR3 and CXCR6, but at lower levels than in colonic lamina propria. A. The gating strategy to detect circulating DP8a cells is shown. B. The frequency within DP8a cells of indicated markers is shown. C. The frequency of the various CCR6, CXCR3 and CXCR6 subsets in blood DP8a is shown for a representative donor and as a mean of 8 donors.

CCR6, CXCR3 and CXCR6 are Potential Markers for Recirculating Colonic DP8α T Cells To characterize circulating DP8a cells for the expression of intestine homing markers and thereby detect gut-associated blood DP8a (see FIG. 2A), PBMCs were stained for not only CCR6, CXCR3 and CXCR6, but also CCR9, CCR10 and b7 (see FIG. 2 B). CCR9 and CCR10 were barely expressed by DP8a cells (or by their CD4 counterparts, not shown). On the other hand, CCR6, CXCR3, CXCR6 or b7 positive cells represented a significant proportion of DP8a cells (20-40%; see FIG. 2 B). Moreover, the expression of these 4 markers in DP8a cells was heterogeneous and overall more frequent than in CD4 T cells (see FIG. 2 B and not shown), which could be compatible with the amount of *F. prau*-specific T cells among circulating DP8a. Indeed, because 1/ the frequency of circulating DP cells can highly vary between individuals and be amplified, especially by viruses, and 2/ the fecal and mucosal *F. prau* levels varies considerably from one person to another, one can speculate that the expected number of *F. prau*-specific T cells within DP8a T cells fluctuates significantly between donors. It was therefore studied more closely the frequency of CCR6, CXCR3, CXCR6 and b7 in DP8a cells. Almost 22% of DP8a cells expressed b7 (FIG. 2 B), but sorted DP8a cells displayed *F. prau*-specific responses in both b7-positive and b7-negative subsets (not shown), eliminating b7 as a marker for *F. prau*-specific DP8a cells.

Based on these results and on the frequent expression of CCR6, CXCR3 and CXCR6 by colon-derived DP8a cells, it was then further focused on CCR6, CXCR3 and CXCR6 as potential markers for *F. prau*-specific DP8a cells: in comparison to LPLs, CCR6+, CXCR6+ and CXCR3+ cells represented only 55%, 32% and 37% respectively of DP8a cells derived from PBMCs, and almost 18% of the latter cells expressed the 3 molecules (see FIG. 2 D). Compared with the co-expression of these three markers by a majority of colon DP8α cells, these data suggested that only a fraction of circulating DP8α T cells could be colon-derived $T_{REGS}$.

*F. prau*-Specific DP8α T Cells Express CCR6 and CXCR6

Figure 3:
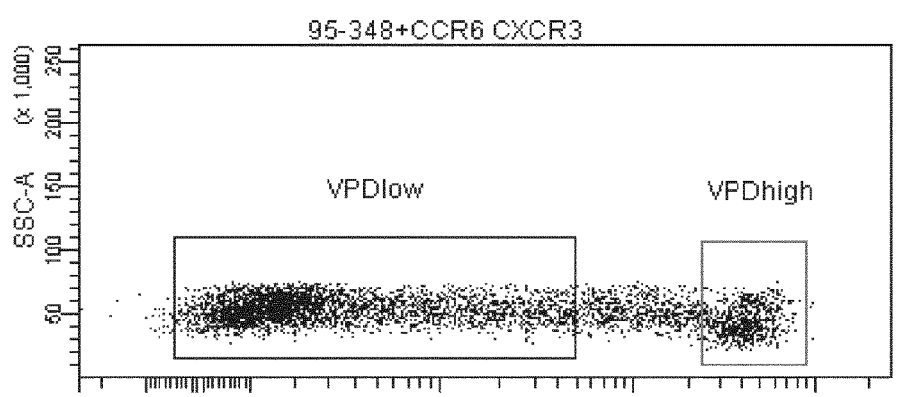
FIG. 3: F. prau-specific DP8a T cells are enriched in CCR6 and CXCR6 cells. $CD4^+$ T cells were stained with VPD and stimulated by autologous monocytes (ratio monocytes:$CD4^+$ T cells of about 1:1) loaded 6 h with F. prau (ratio monocytes:bacteria of about 1:10) in the presence of 0.5 microg/ml anti-CD28 (Miltenyi Biotec). Unloaded monocytes or monocytes in the presence of CD3/CD28 beads (ratio T cells:beads of 3:1) were used as negative and positive controls, respectively. Proliferation was measured at day 5 by dilution of VPD. CCR6 (B) and CXCR6 (C) expression was assessed in proliferated ($VPD^{low}$) versus non-reactive ($VPD^{high}$) DP8a cells (A). Two-sided paired t-test; *: p<0.05 was considered significant.
Figure 3:
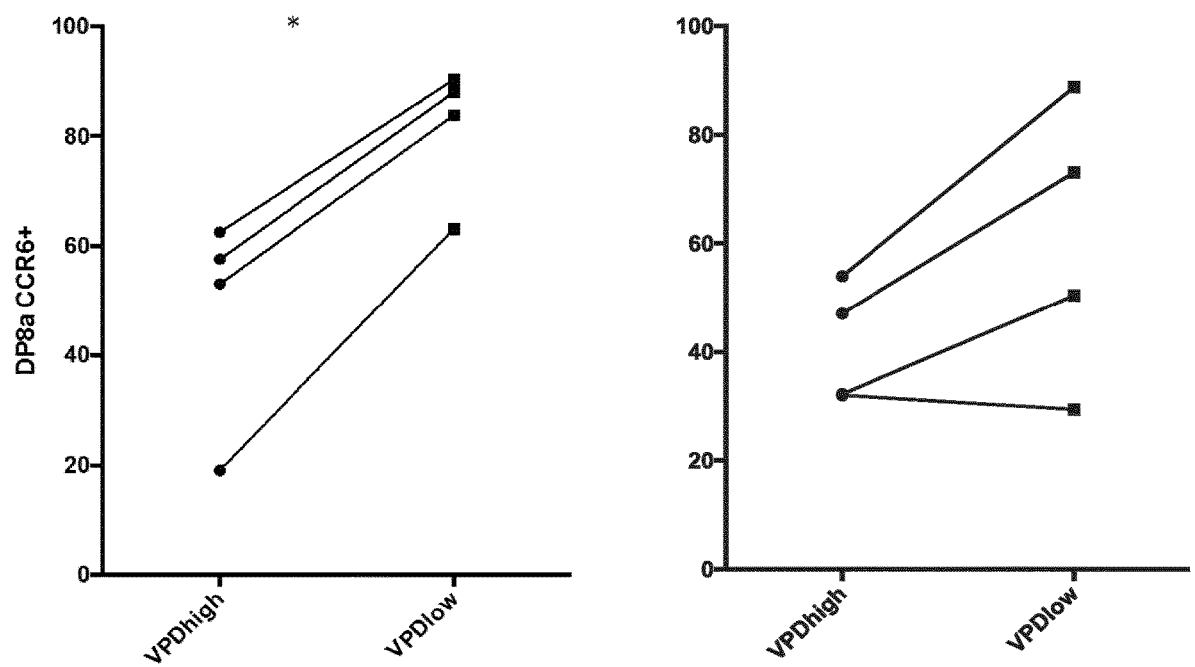

To better determine whether these receptors are preferentially expressed by *F. prau*-specific DP8a, stimulation of VPD-stained CD4+ T cells by autologous monocytes loaded with *F. prau* was performed. Five days later, proliferation to *F. prau* was assessed and CCR expression was studied in proliferated (*F. prau*-specific) versus non-proliferated DP8a cells (see FIG. 3A). CCR6-positive DP8a cells represented a ($p<0.003$; n=4) higher frequency in VPD$^{low}$ (*F. prau*-specific) than in VPD$^{high}$ DP8α cells (see FIG. 3 B). A similar trend was observed for CXCR6 (see FIG. 3 C). In contrast, CXCR3-positive DP8a cells were equally found in VPD$^{high}$ versus VPD$^{low}$ fractions (not shown). Altogether these data suggest that *F. prau*-specific DP8a cells preferentially express CCR6 and CXCR6, but not CXCR3.

Figure 4:
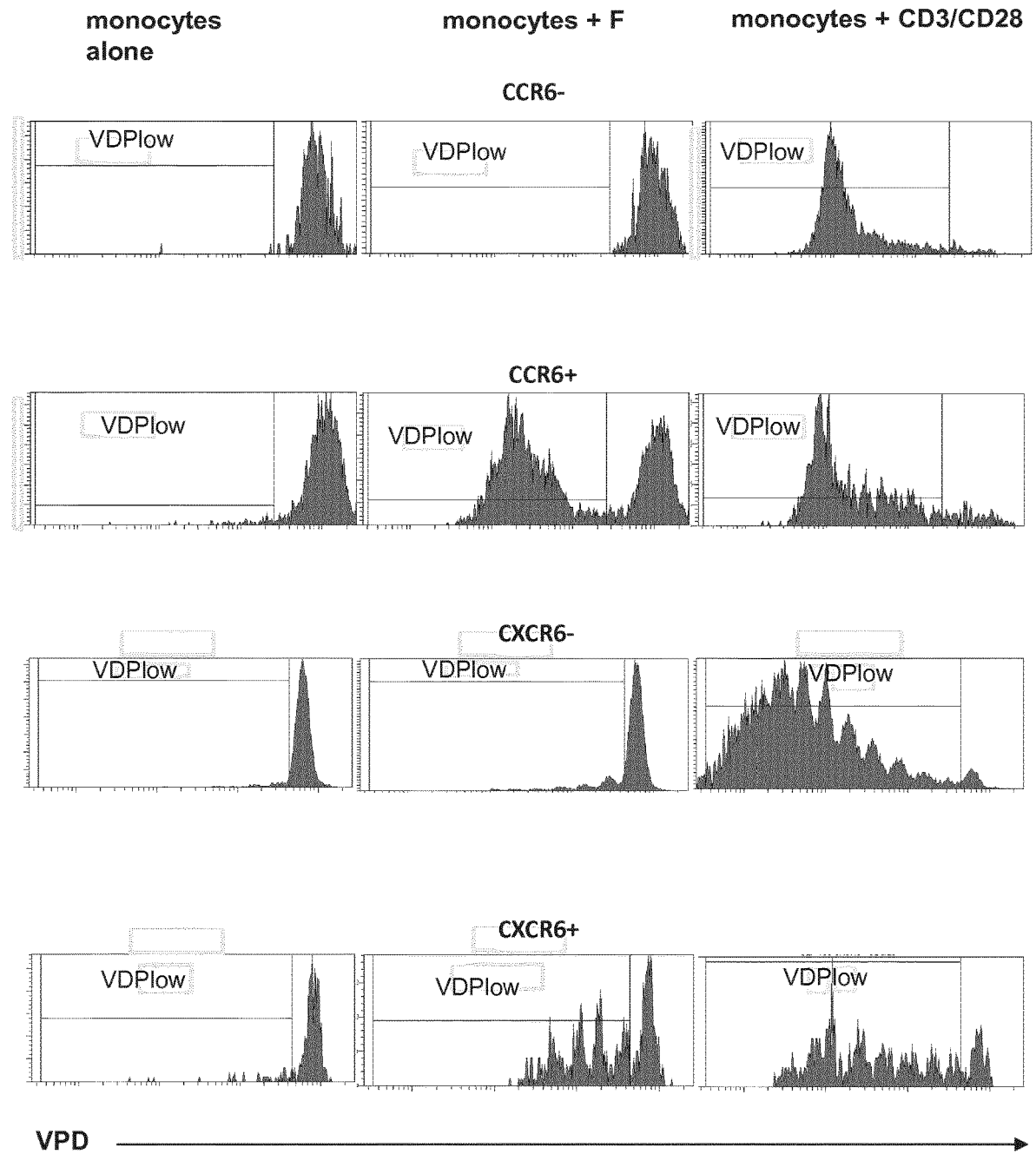
FIG. 4: Circulating F. prau-reactive DP8a cells are present in the CCR6+ population. Sorted CCR6-negative or CCR6-positive, as well as CXCR6-negative and positive DP8a T cells were stained with VPD and stimulated by autologous monocytes (ratio monocytes:DP8a T cells of about 1:1) loaded ON with F. prau (ratio monocytes:bacteria of about 1:10; middle panel) in the presence of 0.5 microg/ml anti-CD28 (Miltenyi Biotec). Unloaded monocytes ("monocytes alone") or monocytes in the presence of CD3/CD28 beads (ratio T cells:beads of 3:1) were used as negative and positive controls, respectively. Proliferation was measured at day 5 by dilution of VPD.

It was further studied the *F. prau*-specificity of both CCR6-negative and CCR6-positive DP8a cells. No *F. prau*-specific cells were detected in the CCR6-negative fraction of DP8a cells (see FIG. 4). Nevertheless, in the same donor, a significant fraction of CCR6-positive DP8a cells proliferated in response to *F. prau*. In other words, *F. prau*-specific cells can be found in the CCR6+ fraction, but not in the CCR6− fraction, of DP8a cells. Similarly, CXCR6-negative DP8α contained only very few *F. prau*-reactive, while the *F. prau*-specific cells were strikingly found in the CXCR6-positive fraction of DP8α cells (See FIG. 4).

Figure 5:
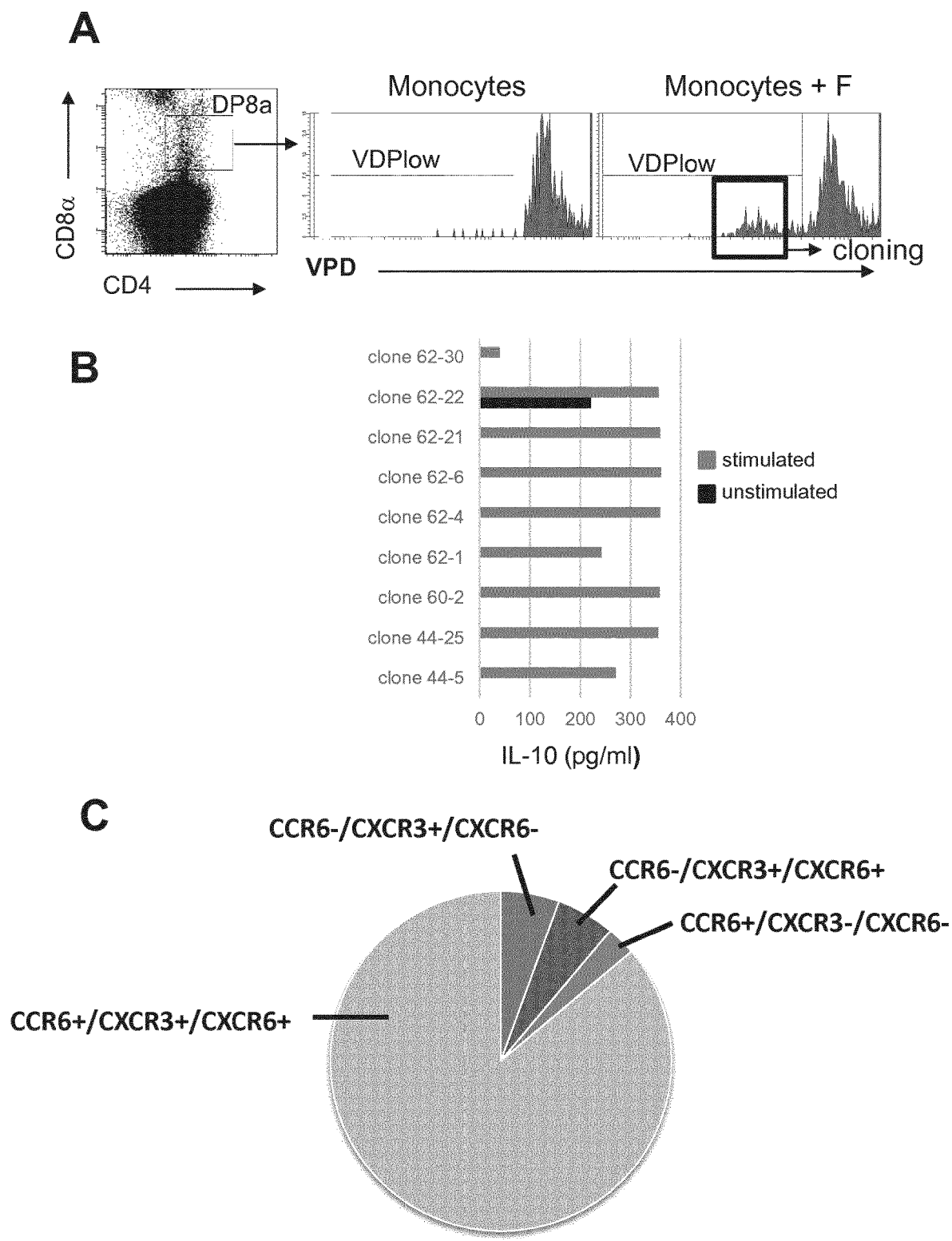
FIG. 5: Clonal responses and phenotype of circulating DP8a cells. A. Gating strategy used for cloning. B. Production of IL-10 by a panel of DP8a clones in the presence (gray bars) or in the absence (black bars) of 1 microg/ml coated anti-CD3 Ab. C. Percentages of clones among all 36 F. prau-specific DP8a clones tested expressing the indicated subsets. Non-indicated subsets were not detected in the clone panel.

To better assess whether *F. prau*-specific cells were located in the CCR6+ and CXCR6+ DP8α subset, clones were generated from an enriched population of specific cells (see FIG. 5A). Thirty-six clones proliferated and produced IFNg in response to autologous monocytes loaded with *F. prau* (data not shown). Additionally, most of these clones produced IL-10 upon CD3 ligation (see FIG. 5 B). Strikingly, the majority (about 86%) of the tested *F. prau*-specific clones expressed CCR6, CXCR3 as well as CXCR6 and 89% and 92% expressed CCR6 and CXCR6, respectively (see FIG. 5 C), highly suggestive of a significant correlation between *F. prau*-specificity and CCR6/CXCR6 expression.

Circulating F-Prau-Specific DP8α Clones Inhibits CD4 T Cell Proliferation

Figure 6:
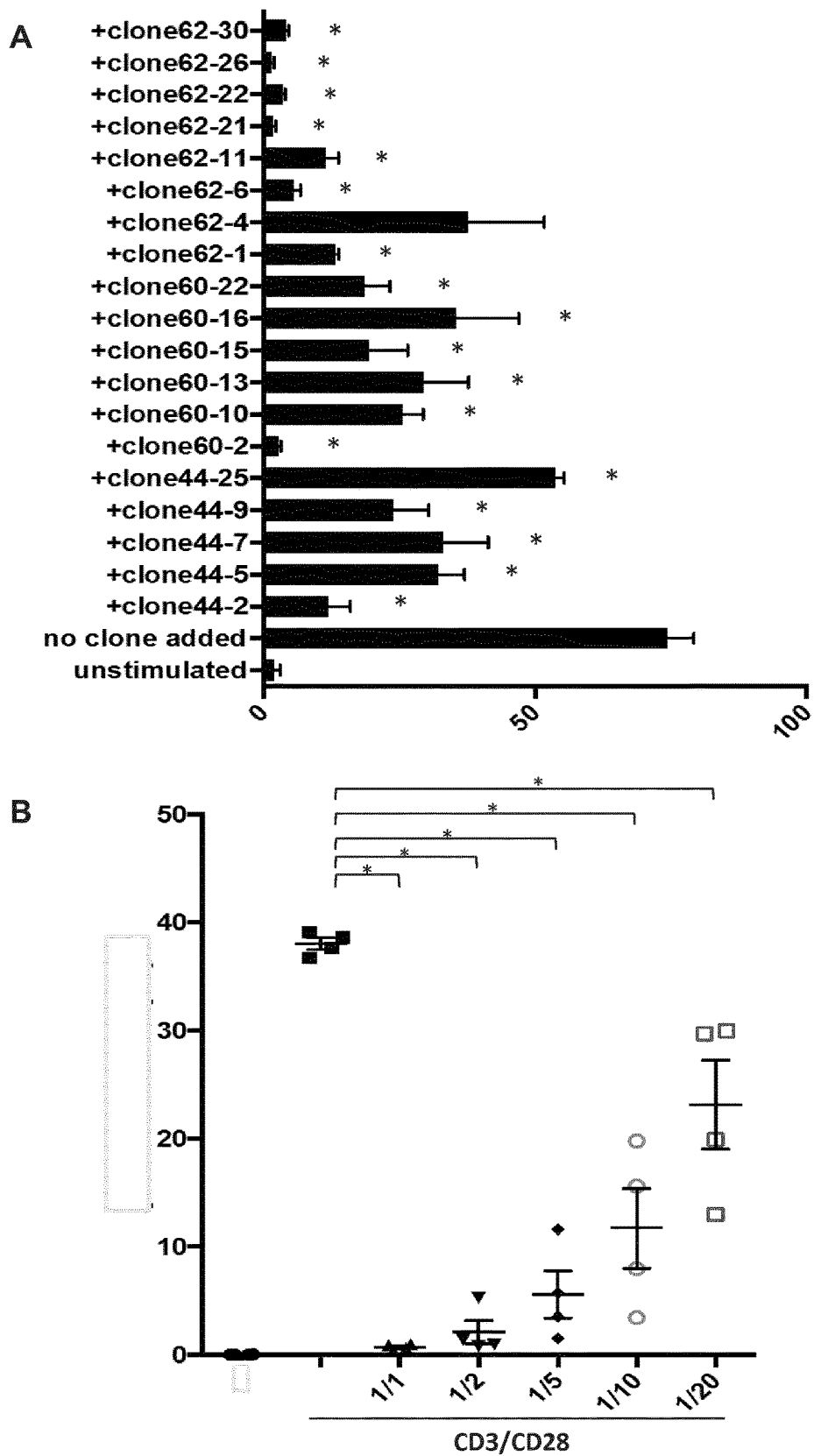
FIG. 6: F-prau-specific DP8a clones inhibit CD4 T cell proliferation. A. $CD4^+$ T cells were stained with VPD and stimulated by CD3/CD28 beads (ratio CD4 T cells:beads of 3:1) in the presence or in the absence of each of all 19 clones tested (ratio 1:1). Proliferation of CD4 T cells was measured at day 5. sem bars are from 3 different donors of CD4 T cells. B. $VPD^+$ CD4 T cells were stimulated as above at indicated CD4 T cells:DP8a clones ratios and proliferation was measured at day 5 in the presence of 4 different DP8a clones. Two-sided unpaired t-test; error bars: sem; *: $p<0.05$ was considered significant.

To determine their inhibitory potential, VPD-stained $CD4^+$ T cells were stimulated by CD3/CD28 beads in the presence or in the absence of one *F. prau*-specific DP8α clone. Most of the 19 tested clones substantially inhibited CD4 T cell proliferation (see FIG. 6A) and still displayed inhibitory functions at 1:20 DP8a:$CD4^+$ T cell ratio (see FIG. 6B), demonstrating their potent regulatory function.

Circulating F-Prau-Specific DP8a Clones Display $T_{R1}$-Like TREG Properties

To establish the TRI-like features of these clones, it was first assessed their ability to produce IL-10. Most of these clones produced IL-10 upon CD3 ligation and stimulation by *F. prau*-loaded monocytes (data not shown). Moreover, $CD4^+$ T cells proliferation induced by CD3/CD28 beads was substantially inhibited in the presence of all the tested clones (data not shown), an inhibition still exhibited at 1:10 DP8α: $CD4^+$ T cell ratio, demonstrating their potent regulatory function. It was also checked for the expression of CD39 and CD73 by the clones, two ectoenzymes, which in cooperation are involved in the differentiation and function of regulatory $T_R1$ cells. *F. prau*-specific DP8α clones expressed CD39 at heightened levels, as compared to $T_H1$ ($CD4^+/CXCR3^+$) or $Foxp3^+$ $T_{REG}$ ($CD4^+/CD25^{high}/CD127^{low}$) clones generated in parallel of DP8α clones. DP8α clones also expressed CD73 on a fraction of their cells, ranging from 5 to 42% of the clone cells. $T_H1$ and $FoxP3^+$ $T_{REG}$ cell clones used also expressed CD73 within this range. RORγ is known to be expressed by gut-derived $T_{REGS}$. It was expressed by the DP8α clones as well as the $FoxP3^+$ $T_{REG}$ clone, as compared to the $T_H1$ clone whose expression was minimal. Because DP8α clones expressed RORγ, it was also assessed whether they produced IL-17. Upon potent stimulation, no IL-17 was detected, confirming their regulatory properties. Finally, while *F. prau*-specific clones lacked CD62L expression, they expressed CD38 therefore exhibiting the $CD62L^-/CD38^+$ phenotype, reported to identify mucosally-differentiated cells.

It was further investigated the underlying mechanism for DP8α regulatory phenotype. It had already been shown that it was partly dependent on IL-10 production, since blocking IL-10 and IL-10R incompletely restored CD4 proliferation. It was also determined that these DP8α clones produced no TGFβ, eliminating a role for this cytokine. It was then assessed whether this mechanism was contact-dependent or not using transwell assays. CD4 proliferation was not inhibited when separated from the DP8α cells by a 1 µm-pore membrane, while clearly inhibited when cells were in the same well. Finally, it was investigated whether CD39 was involved in the regulatory mechanism. Indeed, DP8α clones expressed elevated levels of this membrane-bound molecule. A molecule, POM-1, known to inhibit CD39 function through inhibition of ATP hydrolysis, was used in an assay measuring the inhibition by DP8x clones of CD4 proliferation. Strikingly, in the presence of POM-1, proliferation was significantly restored, demonstrating the implication of CD39 in the regulatory mechanism of DP8α cells. The fact that proliferation was both mostly restored by POM-1 and virtually entirely contact-dependent suggests that IL-10 expression happens downstream of CD39 and may depend on CD39 function, as previously described in dendritic cells.

Circulating $CCR6^+/CXCR6^+$ DP8a Cells are Decreased in IBD Patients

Altogether, these data support that CCR6 and CXCR6 are preferentially expressed by circulating *F. prau*-specific DP8a $T_{REGS}$, which should allow for their quantification/tracking in PBMC samples. The function of these circulating cells seems to mirror those of the colonic lamina propria and it was assessed whether they could help predict colon homeostasis versus inflammation in IBD.

To start assessing a potential role for *F. prau*-specific DP8a $T_{REGS}$ in IBD, the frequency of $CCR6^+/CXCR6^+$ circulating DP8a T cells was determined in 106 IBD patients, as compared to 35 age-matched healthy donors, as well as 12 infectious colitis patients (used as a control for IBD-related inflammation specificity). Strikingly, the frequency of this subset within total $CD3^+$ T cells was significantly (p<0,0001) decreased in IBD patients (mean=$5.9^o/_{ooo}$±1.0), as compared to both that in healthy donors (mean=$24.4^o/_{ooo}$±3.5) or in infectious colitis patients (mean=$49.5^o/_{ooo}$±23.1) (see FIG. 7). The frequency of this subset was also reduced significantly within $CD4^+$ T cells or DP8a cells (data not shown), while the fraction of $CD4^+$ T cells within $CD3^+$ cells was not altered (FIG. 8).

Additionally, it was determined a diagnostic threshold plotting a ROC curve to compare infectious colitis patients versus IBD patients (FIG. 9), which are indiscernible at the time of the first IBD flare. The threshold was positioned at <7.875 $CCR6^+/CXCR6^+$ DP8a cells per 10,000 $CD3^+$ cells, with a sensitivity of 72.22% and a specificity of 100% (Area: 0.931, p<0.0001).

These results show that the frequency of circulating DP8a T cells expressing CCR6 and CXCR6 is decreased in IBD patients, suggesting a role for these cells, or the lack thereof, in the susceptibility to IBD. Moreover, frequencies of these cells in blood are thus of prognosis and diagnosis value, especially at the time of the first IBD flare, which is indiscernible from infectious colitis.

CONCLUSION

The generation of *F. prau*-specific DP8a clones derived from PBMCs definitely established the presence of such cells in the periphery. Importantly, these circulating cells display the same properties than DP8a cells derived from colonic LPLs: they specifically recognize a commensal colonic bacterium, *Faecalibacterium prausnitzii*, produce IL-10 (see FIG. 5) and exert potent regulatory functions (See FIG. 6). Nevertheless, in the colon, most DP8a cells are highly specific for *F. prau*, while in the blood, the frequency of *F. prau*-specific cells varies much more and can be as low as a few percent. This shows that circulating DP8a cells are heterogeneous, in accordance with previous reports that some of these cells represent clonal expansions of various virus-specific T cells, which could take—over *F. prau*-specific DP8a cells. Moreover, the variable frequency of circulating *F. prau*-specific DP8a cells may reflect the highly diverse levels of this bacterium between healthy donors.

In contrast with colonic LPLs, quantifying overall circulating DP8a cells is therefore not sufficient to estimate the frequency of *F. prau*-specific cells, which appears to be central and could represent a marker for IBD. Unfortunately, assessing the specificity of these cells for *F. prau* remains cumbersome because 1/ the bacterium is difficult to grow due to its anaerobic properties and 2/ the need for autologous or HLA-matched antigen presenting cells. Therefore, identification of a marker(s) for *F. prau*-specific DP8a cells is critical to detect these cells in the blood, rather than in colonic biopsies where very little material ends up being available anyway. Therefore, identifying markers for this circulating subset appears to be key to use these cells as a prognosis marker in IBD. Zooming on CCR6- and CXCR6-positive cells within DP8a cells seems to allow for such a closer detection of *F. prau*-specific cells, than overall DP8a cells. Accordingly, *F. prau*-specific cells were found only in the CCR6$^+$ and mainly in the CXCR6$^+$ fractions of DP8a cells (see FIG. 4), as well as 89% and 92% of the clones specific for *F. prau* expressed CCR6 and CXCR6, respectively (see FIG. 5C).

Figure 7:
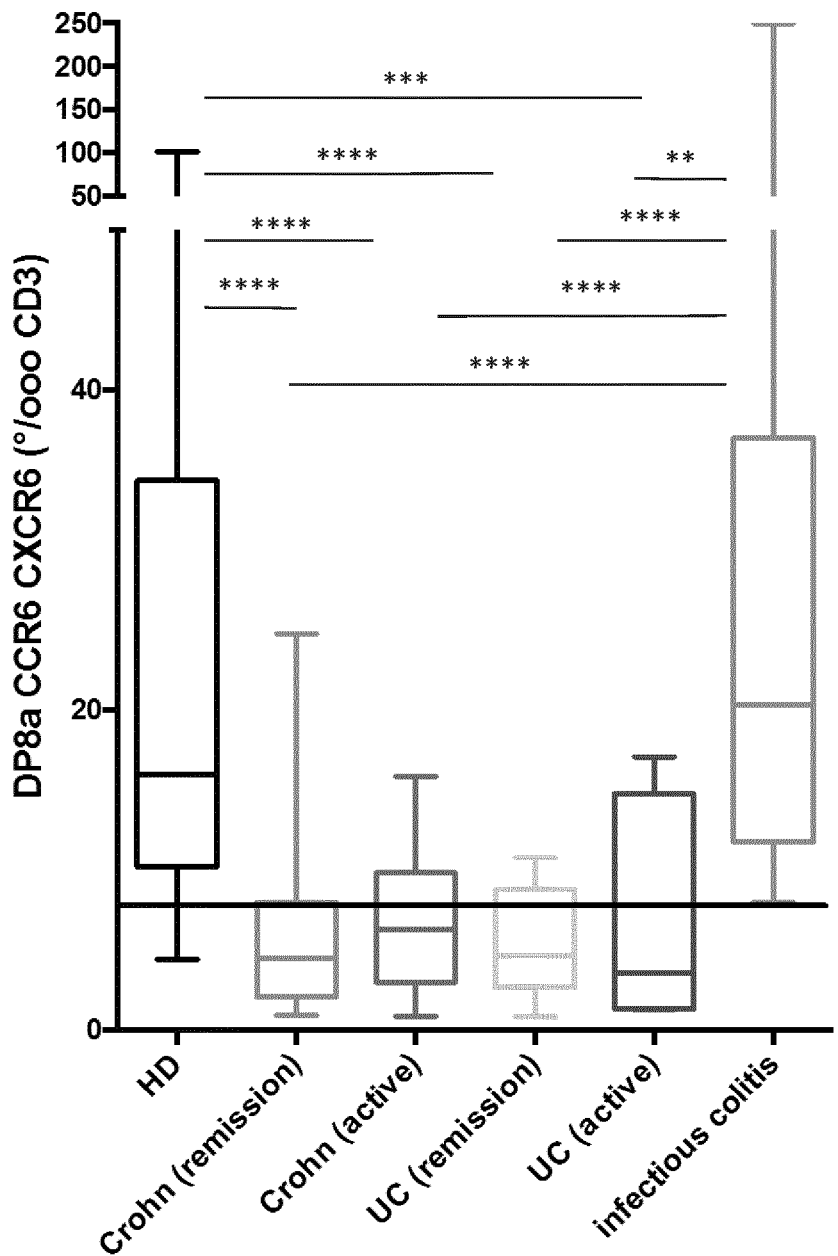
FIGS. 7 and 8: Circulating $CCR6^+/CXCR6^+$ DP8a cells are specifically decreased in IBD patients. PBMCs derived from IBD patients, healthy donors or infectious colitis patients were stained for CD3, CD4, CD8a, CCR6 and CXCR6.
Figure 8:
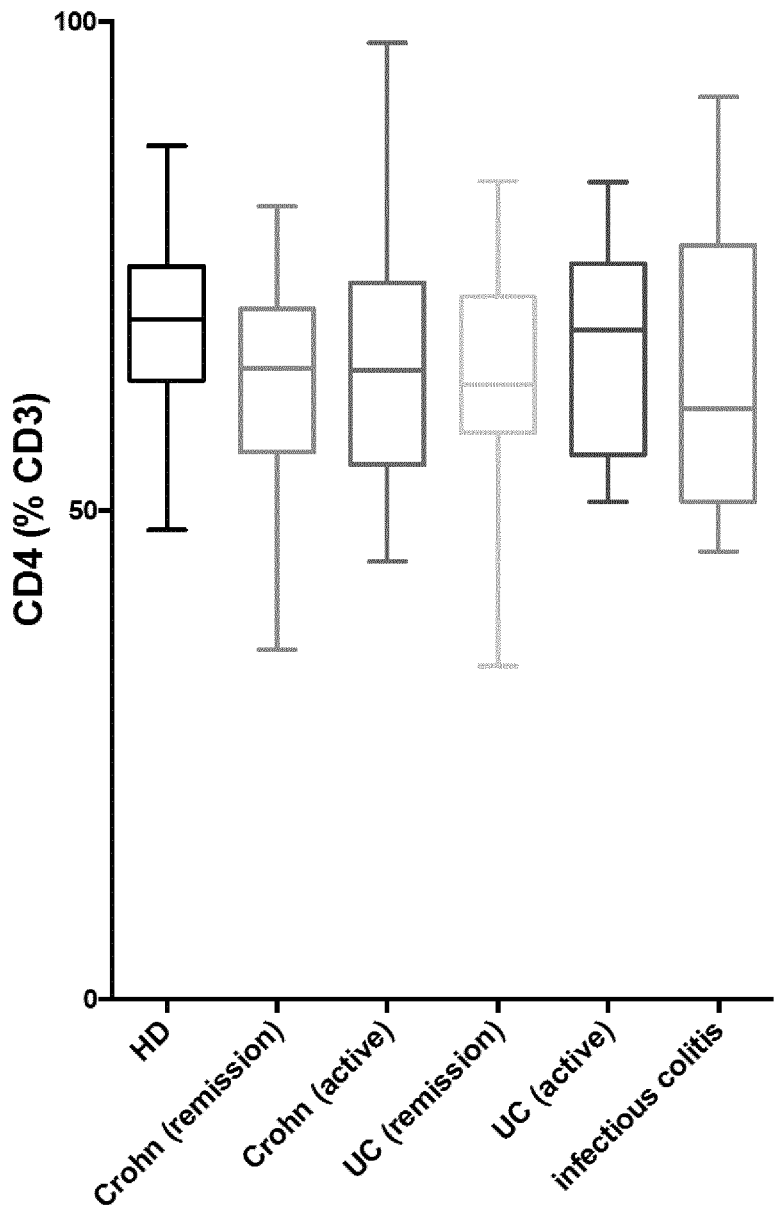
Figure 9:
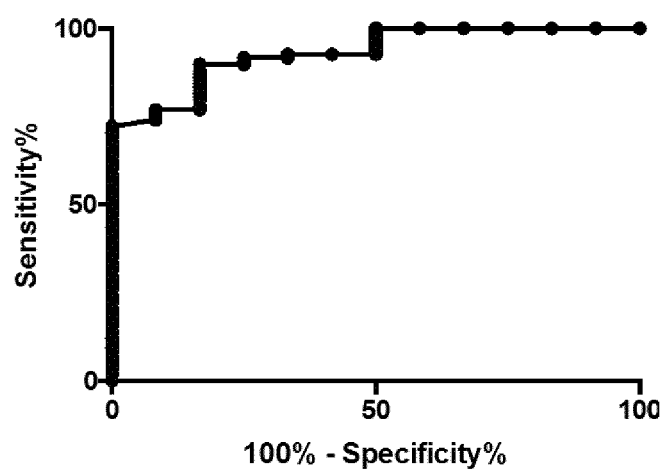
FIG. 9: ROC curve of infectious colitis patients versus IBD patients. This curve was performed using GraphPad Prism version 6.0. and allows for the determination of a diagnostic threshold at <7.875 $CCR6^+/CXCR6^+$ DP8a cells per 10,000 $CD3^+$ cells with a specificity of 100%. The sensitivity is 72.22% (Area: 0.931, $p<0.0001$).

Importantly, the frequency of circulating CCR6$^+$/CXCR6$^+$ DP8a T cells is low in the majority of IBD patients, as compared to age-matched healthy donors (FIGS. 7 to 9). Therefore, a low abundance of these cells in blood is associated with inflammatory gut disorders suggesting that this $T_{REG}$ subset plays a role in the control of IBD-related inflammation. The frequency of these cells in blood is therefore of prognosis/diagnostic value (with a threshold that was positioned at 7.875 CCR6$^+$/CXCR6$^+$ DP8α cells per 10,000 CD3$^+$ T cells), especially at the time of the first IBD flare, which is indiscernible from infectious colitis. Moreover, these results showed no significant differences between remission and relapse groups, suggesting that low DP8a numbers is a general, but specific (since infectious disease patients display a higher DP8a frequency, similar to the one of healthy donors), IBD feature.

T regulatory type 1 ($T_R1$) cells have been described as Foxp3-negative $T_{REG}$ that suppress T cell responses via the secretion of IL-10 and TGF-b. *F. prau*-specific DP8a cells had a strong propensity to produce IL-10 upon TCR ligation (see FIG. 5 C). *F. prau*-specific DP8a cells could therefore be a subset of $T_R1$-like cells. Nevertheless, whether DP8a cells exert their regulatory function through IL-10 still needs to be established. Moreover, *F. prau*-specific DP8α cells differ from described $T_R1$ by their potent proliferative capacity.

Altogether, these data establish 1/ the presence in the blood, of a $T_{REG}$ subset of colon origin induced by *F. prau*, 2/ its variable abundance in healthy subjects and 3/ its striking decrease in IBD patients. Hence, a precise and easy follow-up of circulating DP8a cells is now possible thanks to the identification of their specific expression of both CCR6 and CXCR6. These markers may thus be used as a diagnosis tool.

Example 2: CCR6$^+$/CXCR6$^+$ DP8a T Cells and Obesity

Material and Methods (I) Cell Separation

PBMCs were isolated by Ficoll gradient centrifugation from healthy donor blood (EFS, Nantes, France), or from obese patients suffering or not of type diabetes treated at the CHU of Nantes hospital. This study was approved by the ethics committee of the CHU de Nantes. All patients signed informed consent forms.

(II) Antibodies

For surface staining, cells were harvested, washed and stained for 30 min at 4° C. in PBS 0.1% BSA with the following Abs: anti CD3-PECy7 (clone UCHT1, Becton Dickinson), anti CD4-FITC (clone 13B8.2, Beckman Coulter), anti CD8a-APC (clone B9.11, Beckman Coulter), -BV605 (clone SK1, Becton Dickinson) or -BV421 (clone RPA-T8, Becton Dickinson) CCR6-BV421 (clone 11A9, Becton Dickinson) or -PE (clone G034E3, Biolegend), CXCR3-BV785 (clone G025H7, Biolegend), CXCR6-APC (clone K041E5, Biolegend), anti β7-PE (clone FIB504, Becton Dickinson), Fluorescence was measured on a LSR II flow cytometer and analyzed using Diva software (Becton Dickinson).

(III) Statistical Analysis

Statistical analysis was performed using GraphPad Prism version 6.0. Most comparisons were performed using 2-sided t-test or one-way ANOVA, as indicated in figure legends. p<0.05 was considered statistically significant.

Results

Figure 10:
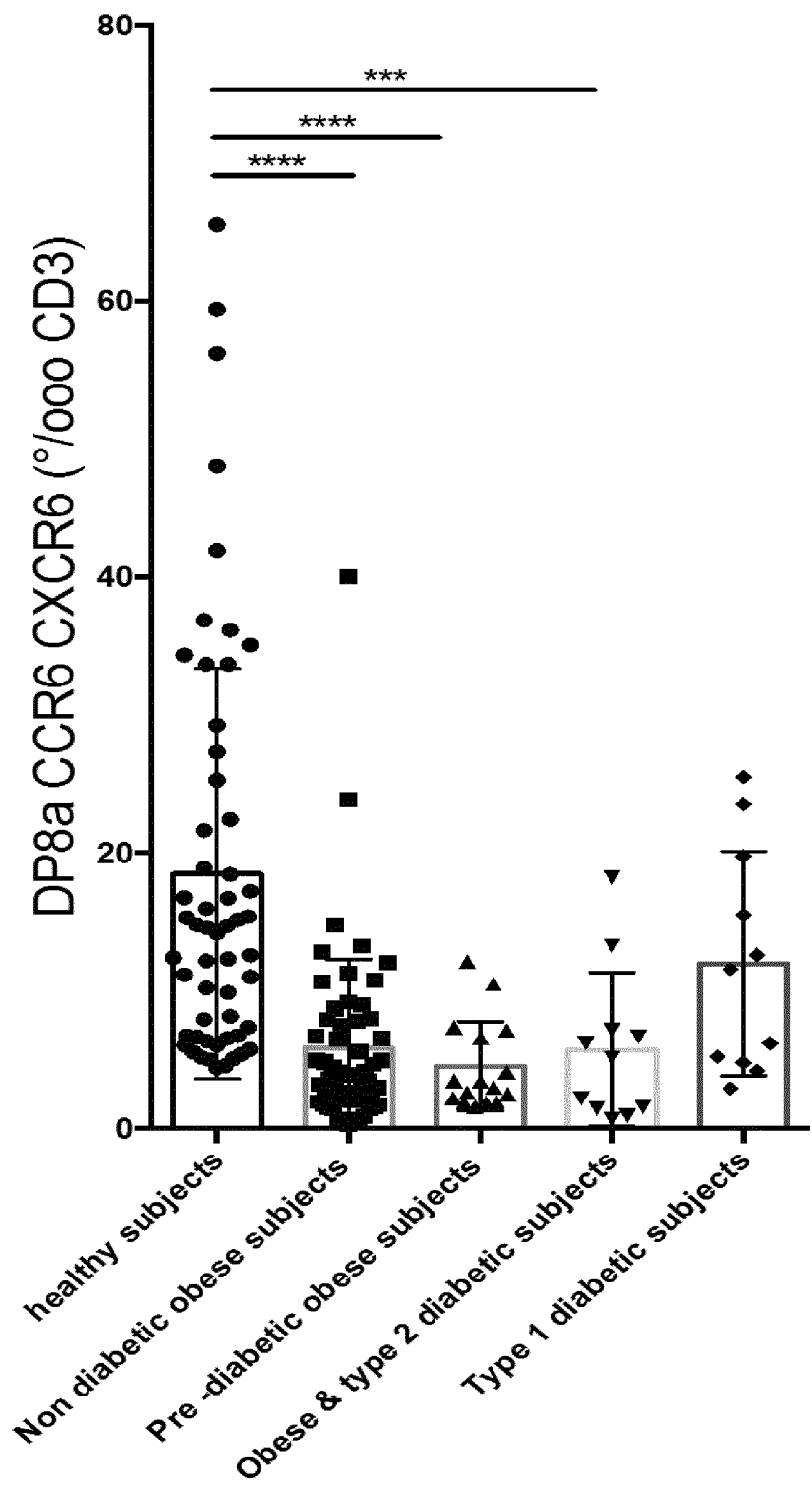
FIG. 10: Circulating $CCR6^+/CXCR6^+$ DP8a cells are significantly decreased in obese patients with or without type 2 diabetes, but not in T1D (Type 1 diabetic) patients. PBMCs derived from healthy donors, non-diabetic obese patients, pre-diabetic obese patients, obese and type 2 diabetic patients or type 1 diabetic patients were stained for CD3, CD4, CD8a, CCR6 and CXCR6.

As shown in FIG. 10, circulating CCR6$^+$/CXCR6$^+$ DP8a cells are significantly decreased in obese patients with or without type 2 diabetes, but not in T1D patients (Type 1 diabetic patients). This population of cells is therefore useful in the methods according to the invention, wherein the disease associated with a decrease of *F. prausnitzii* is obesity.

The invention claimed is:

1. A method of treating a subject afflicted with a disease characterized by a decrease of F. prausnitzii, wherein said method comprises:
   a) determining the number and/or concentration and/or proportion of T lymphocytes with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype, in a biological sample from the subject, optionally, comparing the result of step a) with i) a control standard value corresponding to the number and/or concentration and/or proportion of these T lymphocytes typically found in a biological sample of the same nature from a healthy subject, and/or ii) a control standard value corresponding to the number and/or concentration and/or proportion of these T lymphocytes typically found in a biological sample of the same nature from a patient suffering from said disease characterized by a decrease of F. prausnitzii;
   b) deducting from the result(s) of step a) and/or step b) where appropriate, if the subject is afflicted with a disease characterized by a decrease of F. prausnitzii, and
   c) administering a suitable treatment to the subject deduced in step c) to be afflicted with a disease characterized by a decrease of F. prausnitzii, wherein said suitable treatment is selected from the group consisting of an immunosuppressant, a probiotic, an antibiotic, F. prausnitzii, a fragment of F. prausnitzii, a pharmaceutical composition comprising isolated T lymphocytes with a CD4+ CD8αα$^{low}$ CCR6+ phenotype, a CD4+ CD8αα$^{low}$ CXCR6+ phenotype and/or a CD4+ CD8αα$^{low}$ CCR6+ CXCR6+ phenotype and their combinations.

2. The method according to claim 1, wherein the disease characterized by a decrease of F. prausnitzii is an inflammatory bowel disease (IBD).

3. The method according to claim 1, wherein the biological sample is a blood sample.

* * * * *

UNITED STATES PATENT AND TRADEMARK OFFICE
CERTIFICATE OF CORRECTION

| | | |
|---|---|---|
| PATENT NO. | : 12,405,267 B2 | Page 1 of 1 |
| APPLICATION NO. | : 17/059315 | |
| DATED | : September 2, 2025 | |
| INVENTOR(S) | : Altare et al. | |

It is certified that error appears in the above-identified patent and that said Letters Patent is hereby corrected as shown below:

In the Claims

Claim 1 in Column 37, Line 40 to Column 38, Line 52 should read as follows:
1. A method of treating a subject afflicted with a disease characterized by a decrease of F. prausnitzii, wherein said method comprises:
    a) determining the number and/or concentration and/or proportion of T lymphocytes with a CD4+ CD8ααlow CCR6+ phenotype, a CD4+ CD8ααlow CXCR6+ phenotype and/or a CD4+ CD8ααlow CCR6+ CXCR6+ phenotype, in a biological sample from the subject, optionally, comparing the result of step a) with i) a control standard value corresponding to the number and/or concentration and/or proportion of these T lymphocytes typically found in a biological sample of the same nature from a healthy subject, and/or ii) a control standard value corresponding to the number and/or concentration and/or proportion of these T lymphocytes typically found in a biological sample of the same nature from a patient suffering from said disease characterized by a decrease of F. prausnitzii;
    b) deducting from the result(s) of step a) if the subject is afflicted with a disease characterized by a decrease of F. prausnitzii, and
    c) administering a suitable treatment to the subject deduced in step b) to be afflicted with a disease characterized by a decrease of F. prausnitzii, wherein said suitable treatment is selected from the group consisting of an immunosuppressant, a probiotic, an antibiotic, F. prausnitzii, a fragment of F. prausnitzii, a pharmaceutical composition comprising isolated T lymphocytes with a CD4+ CD8ααlow CCR6+ phenotype, a CD4+ CD8ααlow CXCR6+ phenotype and/or a CD4+ CD8ααlow CCR6+ CXCR6+ phenotype and their combinations.

Signed and Sealed this
Fourteenth Day of October, 2025

John A. Squires
*Director of the United States Patent and Trademark Office*

SEQUENCE LISTING

<160> NUMBER OF SEQ ID NOS: 2

<210> SEQ ID NO 1
<211> LENGTH: 344
<212> TYPE: PRT
<213> ORGANISM: Homo sapiens

<400> SEQUENCE: 1

```
Met Ala Asn Tyr Thr Leu Ala Pro Glu Asp Glu Tyr Asp Val Leu Ile
1               5                   10                  15

Glu Gly Glu Leu Glu Ser Asp Glu Ala Glu Gln Cys Asp Lys Tyr Asp
            20                  25                  30

Ala Gln Ala Leu Ser Ala Gln Leu Val Pro Ser Leu Cys Ser Ala Val
        35                  40                  45

Phe Val Ile Gly Val Leu Asp Asn Leu Leu Val Val Leu Ile Leu Val
    50                  55                  60

Lys Tyr Lys Gly Leu Lys Arg Val Glu Asn Ile Tyr Leu Leu Asn Leu
65                  70                  75                  80

Ala Val Ser Asn Leu Cys Phe Leu Leu Thr Leu Pro Phe Trp Ala His
                85                  90                  95
```

```
Ala Gly Gly Asp Pro Met Cys Lys Ile Leu Ile Gly Leu Tyr Phe Val
            100                 105                 110

Gly Leu Tyr Ser Glu Thr Phe Phe Asn Cys Leu Leu Thr Val Gln Arg
        115                 120                 125

Tyr Leu Val Phe Leu His Lys Gly Asn Phe Phe Ser Ala Arg Arg Arg
    130                 135                 140

Val Pro Cys Gly Ile Ile Thr Ser Val Leu Ala Trp Val Thr Ala Ile
145                 150                 155                 160

Leu Ala Thr Leu Pro Glu Tyr Val Val Tyr Lys Pro Gln Met Glu Asp
                165                 170                 175

Gln Lys Tyr Lys Cys Ala Phe Ser Arg Thr Pro Phe Leu Pro Ala Asp
            180                 185                 190

Glu Thr Phe Trp Lys His Phe Leu Thr Leu Lys Met Asn Ile Ser Val
        195                 200                 205

Leu Val Leu Pro Leu Phe Ile Phe Thr Phe Leu Tyr Val Gln Met Arg
    210                 215                 220

Lys Thr Leu Arg Phe Arg Glu Gln Arg Tyr Ser Leu Phe Lys Leu Val
225                 230                 235                 240

Phe Ala Ile Met Val Val Phe Leu Leu Met Trp Ala Pro Tyr Asn Ile
                245                 250                 255

Ala Phe Phe Leu Ser Thr Phe Lys Glu His Phe Ser Leu Ser Asp Cys
            260                 265                 270

Lys Ser Ser Tyr Asn Leu Asp Lys Ser Val His Ile Thr Lys Leu Ile
        275                 280                 285

Ala Thr Thr His Cys Cys Ile Asn Pro Leu Leu Tyr Ala Phe Leu Asp
    290                 295                 300

Gly Thr Phe Ser Lys Tyr Leu Cys Arg Cys Phe His Leu Arg Ser Asn
305                 310                 315                 320

Thr Pro Leu Gln Pro Arg Gly Gln Ser Ala Gln Gly Thr Ser Arg Glu
                325                 330                 335

Glu Pro Asp His Ser Thr Glu Val
            340

<210> SEQ ID NO 2
<211> LENGTH: 342
<212> TYPE: PRT
<213> ORGANISM: Homo sapiens

<400> SEQUENCE: 2

Met Ala Glu His Asp Tyr His Glu Asp Tyr Gly Phe Ser Ser Phe Asn
1               5                   10                  15

Asp Ser Ser Gln Glu Glu His Gln Asp Phe Leu Gln Phe Ser Lys Val
                20                  25                  30

Phe Leu Pro Cys Met Tyr Leu Val Phe Val Cys Gly Leu Val Gly
            35                  40                  45

Asn Ser Leu Val Leu Val Ile Ser Ile Phe Tyr His Lys Leu Gln Ser
        50                  55                  60

Leu Thr Asp Val Phe Leu Val Asn Leu Pro Leu Ala Asp Leu Val Phe
65                  70                  75                  80

Val Cys Thr Leu Pro Phe Trp Ala Tyr Ala Gly Ile His Glu Trp Val
                85                  90                  95

Phe Gly Gln Val Met Cys Lys Ser Leu Leu Gly Ile Tyr Thr Ile Asn
            100                 105                 110

Phe Tyr Thr Ser Met Leu Ile Leu Thr Cys Ile Thr Val Asp Arg Phe
        115                 120                 125
```

```
                    -continued

Ile Val Val Val Lys Ala Thr Lys Ala Tyr Asn Gln Gln Ala Lys Arg
    130                 135                 140

Met Thr Trp Gly Lys Val Thr Ser Leu Leu Ile Trp Val Ile Ser Leu
145                 150                 155                 160

Leu Val Ser Leu Pro Gln Ile Ile Tyr Gly Asn Val Phe Asn Leu Asp
                165                 170                 175

Lys Leu Ile Cys Gly Tyr His Asp Glu Ala Ile Ser Thr Val Val Leu
            180                 185                 190

Ala Thr Gln Met Thr Leu Gly Phe Phe Leu Pro Leu Leu Thr Met Ile
        195                 200                 205

Val Cys Tyr Ser Val Ile Ile Lys Thr Leu Leu His Ala Gly Gly Phe
    210                 215                 220

Gln Lys His Arg Ser Leu Lys Ile Ile Phe Leu Val Met Ala Val Phe
225                 230                 235                 240

Leu Leu Thr Gln Met Pro Phe Asn Leu Met Lys Phe Ile Arg Ser Thr
                245                 250                 255

His Trp Glu Tyr Tyr Ala Met Thr Ser Phe His Tyr Thr Ile Met Val
            260                 265                 270

Thr Glu Ala Ile Ala Tyr Leu Arg Ala Cys Leu Asn Pro Val Leu Tyr
        275                 280                 285

Ala Phe Val Ser Leu Lys Phe Arg Lys Asn Phe Trp Lys Leu Val Lys
    290                 295                 300

Asp Ile Gly Cys Leu Pro Tyr Leu Gly Val Ser His Gln Trp Lys Ser
305                 310                 315                 320

Ser Glu Asp Asn Ser Lys Thr Phe Ser Ala Ser His Asn Val Glu Ala
                325                 330                 335

Thr Ser Met Phe Gln Leu
                340
```